United States Patent
Le Greneur et al.

(10) Patent No.: US 11,426,470 B2
(45) Date of Patent: *Aug. 30, 2022

(54) COMPLEX OF GADOLINIUM AND A CHELATING LIGAND DERIVED OF A DIASTEREOISOMERICALLY ENRICHED PCTA AND SYNTHESIS METHOD

(71) Applicant: GUERBET, Villepinte (FR)

(72) Inventors: Soizic Le Greneur, Bures-sur-Yvette (FR); Alain Chénedé, Lagord (FR); Martine Cerf, Breuil-Magné (FR); Stéphane Decron, Marans (FR); Bruno François, Saint-Jean-de-Liversay (FR)

(73) Assignee: GUERBET, Villepinte (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/397,022

(22) Filed: Aug. 9, 2021

(65) Prior Publication Data

US 2021/0361782 A1 Nov. 25, 2021

Related U.S. Application Data

(63) Continuation of application No. 17/423,589, filed as application No. PCT/EP2020/051142 on Jan. 17, 2020.

(30) Foreign Application Priority Data

Jan. 17, 2019 (FR) ...................... 1900433

(51) Int. Cl.
| | | |
|---|---|---|
| *A61B 5/055* | (2006.01) | |
| *A61K 49/10* | (2006.01) | |
| *C07D 471/08* | (2006.01) | |
| *C07F 5/00* | (2006.01) | |

(52) U.S. Cl.
CPC .......... *A61K 49/106* (2013.01); *C07D 471/08* (2013.01); *C07F 5/003* (2013.01)

(58) Field of Classification Search
CPC ...... A61K 49/106; C07D 471/08; C07F 5/003
See application file for complete search history.

(56) References Cited

U.S. PATENT DOCUMENTS

| | | |
|---|---|---|
| 6,440,956 B1 | 8/2002 | Guerbet |
| 8,114,863 B2 | 2/2012 | Guerbet |
| 10,973,934 B2 | 4/2021 | Napolitano et al. |

FOREIGN PATENT DOCUMENTS

| | | |
|---|---|---|
| EP | 0 481 420 A1 | 10/1991 |
| EP | 0 992 245 A1 | 9/1998 |
| EP | 1 931 673 B1 | 10/2006 |
| EP | 2 988 756 B1 | 4/2014 |

OTHER PUBLICATIONS

International Search Report and Written Opinion, issued from the European Patent Office, in corresponding International Application No. PCT/EP2020/051142, dated Mar. 20, 2020 (4 pages).

(Continued)

*Primary Examiner* — Michael G. Hartley
*Assistant Examiner* — Melissa J Perreira
(74) *Attorney, Agent, or Firm* — Finnegan, Henderson, Farabow, Garrett & Dunner, L.L.P.

(57) ABSTRACT

The present invention relates to a complex of formula (II) constituted of at least 80% of a diastereoisomeric excess comprising a mixture of isomers II-RRR and II-SSS of formulae:

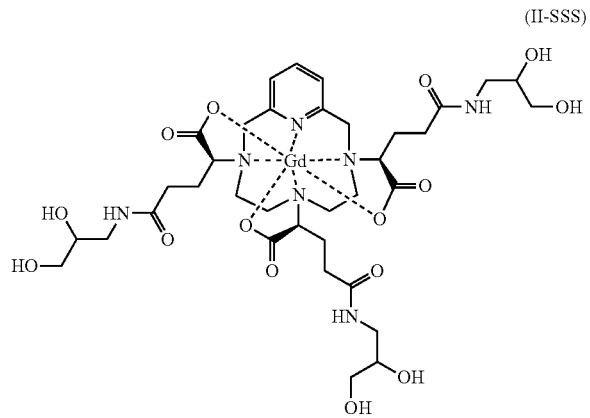

(II-SSS)

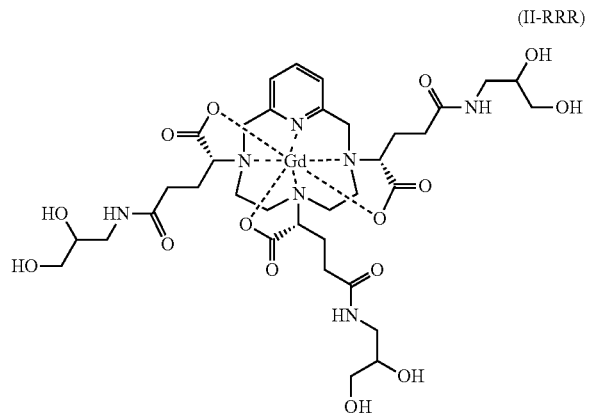

(II-RRR)

The present invention also relates to a process for preparing said complex of formula (II), and also to two synthetic intermediates.

16 Claims, 1 Drawing Sheet

(56) References Cited

OTHER PUBLICATIONS

International Search Report and Written Opinion, issued from the European Patent Office, in corresponding International Application No. PCT/EP2020/051153, dated Apr. 6, 2020 (4 pages).
Aime, Silvio et al., "Solution and Solid-State Characterization of Highly Rigid, Eight-Coordinate Lanthanide(III) Complexes of a Macrocyclic Tetrabenzylphosphinate," *Inorg. Chem.* 1994, 33, 4696-4706 (11 pages).
Aime, Silvio et al., "Lanthanide(III) chelates for NMR biomedical applications," *Chemical Society Reviews*, 1998, vol. 27, 19-29 (11 pages).
Aime, Silvio et al., "NMR, Relaxometric, and Structural Studies of the Hydration and Exchange Dynamics of Cationic Lanthanide Complexes of Macrocyclic Tetraamide Ligands," *J. Am. Chem. Soc.* 1999, 121, 5762-5771 (10 pages).
Aime, Silvio et al., "Properties, Solution State Behavior, and Crystal Structures of Chelates of DOTMA," *Inorg Chem.* Sep. 5, 2011; 50(17): 7955-7965 (11 pages).
Bianchi, Antonio et al., "Thermodynamic and structural properties of $Gd^{3+}$ complexes with functionalized macrocyclic ligands based upon 1,4,7,10-tetraazacyclododecane," *J. Chem. Soc., Dalton Trans.*, 2000, 697-705 (9 pages).
Brittain, H. G. et al., "Luminescence and NMR Studies of the Conformational Isomers of Lanthanide Complexes with an Optically Active Polyaza Polycarboxylic Macrocycle," *Inorg Chem.*, 1984, 23(26), 4459-4466 (8 pages).
Brücher, Ernö, "Kinetic Stabilities of Gadolinium(III) Chelates Used as MRI Contrast Agents," *Topics in Current Chemistry*, 2002, vol. 221, 104-122 (20 pages).
Caravan, Peter, "Strategies for increasing the sensitivity of gadolinium based MRI contrast agents," *Chem. Soc. Rev.*, 2006, 35, 512-523 (12 pages).
Chan Kannie Wai-Yan et al, "Small molecular gadolinium(III) complexes as MRI contrast agents for diagnostic imaging," *Coordination Chemistry Reviews*, 251 (2007) 2428-2451 (24 pages).
Clough, Thomas J et al., "Ligand design strategies to increase stability of gadolinium-based magnetic resonance imaging contrast agents," *Nature Communications*, (2019) 10:1420 (14 pages).
Comblin, Vinciane et al., "Designing new MRI contrast agents: a coordination chemistry challenge," *Coordination Chemistry Reviews* 185-186 (1999) 451-470 (20 pages).
Dai Lixiong et al., "Chiral DOTA chelators as an improved platform for biomedical imaging and therapy applications," *Nature Communications*, (2018) 9:857 (10 pages).
Dai Lixiong et al., "Synthesis of Water-Soluble Chiral DOTA Lanthanide Complexes with Predominantly Twisted Square Antiprism Isomers and Circularly Polarized Luminescence," *Inorg. Chem.* 2019, 58, 12506-12510 (5 pages).
Di Bari, Lorenzo et al., "Solution Equilibria in YbDOTMA, a Chiral Analogue of One of the Most Successful Contrast Agents for MRI, GdDOTA," *Eur. J. Inorg. Chem.* 2000, 75-82 (8 pages).
Di Bari, Lorenzo et al., "Structural and Chiroptical Properties of the Two Coordination Isomers of YbDOTA-Type Complexes," *Inorg. Chem.* 2005, vol. 44, No. 23, 8391-8398 (8 pages).
Di Bari, Lorenzo et al., Static and Dynamic Stereochemistry of Chiral Ln DOTA Analogues, *ChemPhysChem* 2011, 12, 1490-1497 (8 pages).
Dunand, Frank A. et al., "First $^{17}O$ NMR Observation of Coordinated Water on Both Isomers of $[Eu(DOTAM)(H_2O)]^{3+}$: A Direct Access to Water Exchange and its Role in the Isomerization," *J. Am. Chem. Soc.* 2000, 122, 1506-1512 (7 pages).
Elemento, Elisa (2008), "New gadolinium contrast agents for MRI," Durham theses, Durham University, (249 pages).
Fossheim, R et al., "Molecular modelling of tetrahydroxymethyl-substituted DOTA derivatives and their Gd(III) ion complexes," *Eur J Med Chem* (1995) 30, 539-546 (8 pages).
Hermann, Petr et al., "Gadolinium(III) complexes as MRI contrast agents: ligand design and properties of the complexes," *Dalton Trans.*, 2008, 3027-3047 (21 pages).

Howard, Judith A. K. et al., "Structure and dynamics of all of the stereoisomers of europium complexes of tetra(carboxyethyl) derivatives of dota: ring inversion is decoupled from cooperative arm rotation in the RRRR and RRRS isomers," *Chem. Commun.*, 1998, 1381-1382 (2 pages).
Kang, Sang I. et al., "Synthesis, Characterization, and Crystal Structure of the Gadolinium(III) Chelate of (1R,4R,7R)-α,α',α"—Trimethyl-1,4,7,10-tetraazacyclododecane-1,4,7-triacetic Acid (DO3MA)," *Inorg. Chem.* 1993, 32, 2912-2918 (7 pages).
Kotková, Zuzana et al., "Lanthanide(III) Complexes of Phosphorus Acid Analogues of H4DOTA as Model Compounds for the Evaluation of the Second-Sphere Hydration," *Eur. J. Inorg. Chem.* 2009, 119-136 (18 pages).
Kumas, Cemile et al., "Unexpected Changes in the Population of Coordination Isomers for the Lanthanide Ion Complexes of DOTMA-Tetraglycinate," *Inorg. Chem.* 2016, 55, 9297-9305 (9 pages).
Lattuada Luciano et al., "Enhanced relaxivity of $Gd^{III}$-complexes with HP-DO3A-like ligands upon the activation of the intramolecular catalysis of the prototropic exchange," *Inorg. Chem. Front.*, 2021, 8, 1500-1510 (11 pages).
Law, Ga-lai,, "Chiral Cyclen Compounds and Their Uses," The Hong Kong Polytechnic University, Innovation and Technology Development Office, LH-R021/20180424 (1 page).
Lee, Yong-Sok et al., "Origin of the Isomer Stability of Polymethylated DOTA Chelates Complexed with $Ln^{3+}$ Ions," *Eur. J. Inorg. Chem.* 2021, 1428-1440 (13 pages).
Lelli, Moreno et al., "Monitoring proton dissociation and solution conformation of chiral ytterbium complexes with near-IR CD," *Chirality* 17:201-211, 2005 (11 pages).
Lohrke, Jessica et al., "25 Years of Contrast-Enhanced MRI: Developments, Current Challenges and Future Perspectives," *Adv Ther* (2016) 33:1-28 (28 pages).
Lowe, Mark P. et al., "pH-Dependent Modulation of Relaxivity and Luminescence in Macrocyclic Gadolinium and Europium Complexes Based on Reversible Intramolecular Sulfonamide Ligation," *J. Am. Chem. Soc.* 2001, 123, 7601-7609 (9 pages).
Marques, M.P.M. et al., "NMR conformational study of the lanthanide(III) complexes of DOTA in aqueous solution," *Journal of Alloys and Compounds* 225 (1995) 303-307 (5 pages).
McMurry, Thomas J. et al., "Physical Parameters and Biological Stability of Yttrium(III) Diethylenetriaminepentaacetic Acid Derivative Conjugates," *J. Med. Chem.* 1998, 41, 3546-3549 (4 pages).
Messeri, Dimitri, "Targeted and high relaxivity contrast agents," Durham theses, Durham University (2001) (148 pages).
Messeri, Dimitri et al., "A stable, high relaxivity, diaqua gadolinium complex that suppresses anion and protein binding," *Chem. Commun.*, 2001, 2742-2743 (2 pages).
Miller, Kyle J. et al., "The Population of SAP and TSAP Isomers in Cyclen-Based Lanthanide(III) Chelates Is Substantially Affected by Solvent," *Inorg. Chem.* 2010, 49, 8662-8664 (3 pages).
Moreau, Juliette et al., "Thermodynamic and Structural Properties of $Eu^{3+}$, $Gd^{3+}$ and $Tb^{3+}$ Complexes with 1,4,7,10-Tetra(2-glutaryl)-1,4,7,10-tetraazacyclododecane in Solution: EXAFS, Luminescence, Potentiometric Studies, and Quantum Calculations," *Eur. J. Inorg. Chem.* 2003, 3007-3020 (14 pages).
Woods, Mark et al., "Crystal Structures of DOTMA Chelates from $Ce^{3+}$ to $Yb^{3+}$: Evidence for a Continuum of Metal Ion Hydration States," *Chem. Eur. J.* 2019, 25, 9997-10005 (9 pages).
Opina, Ana Christina L. et al., "Analysis of the isomer ratios of polymethylated-DOTA complexes and the implications on protein structural studies," *Dalton Trans.* Mar. 21, 2016; 45(11): 4673-4687(15 pages).
Parker, David et al., "Being Excited by Lanthanide Coordination Complexes: Aqua Species, Chirality, Excited-State Chemistry, and Exchange Dynamics," *Chem. Rev.* 2002, 102, 1977-2010 (34 pages).
Parker, David, "Rare Earth Coordination Chemistry in Action: Exploring the Optical and Magnetic Properties of the Lanthanides in Bioscience While Challenging Current Theories," In: Bünzli, J.-C.G. et al., *Handbook on the Physics and Chemistry of Rare Earths*, 2016, vol. 50, chapter 291 pp. 269-299 (31 pages).
Payne, Katherine M. et al., "Picture of a chelate in exchange: the crystal structure of NaHoDOTMA, a 'semi'-hydrated chelate," *Chem. Commun.*, 2013, 49, 2320-2322 (3 pages).

(56) References Cited

OTHER PUBLICATIONS

Pereira, Giovannia A. et al., "NMR Characterization of Lanthanide(3+) Complexes of Tetraazatetrakisphosphinato and Tetraazatetrakisphosphonato Ligands," *Helvetica Chimica Acta*—vol. 92 (2009) 2532-2551 (20 pages).

Peters, Joop A. et al., "The chemical consequences of the gradual decrease of the ionic radius along the Ln-series," *Coordination Chemistry Reviews* 406 (2020) 213146 (27 pages).

Port, Marc et al., "Synthesis and Physicochemical Characterization of 1,4,7,10-Tetra (2-glutaryl)-1,4,7,10 tetraazacyclododecane Lanthanide Complexes," *Acad Radiol* 2002, 9(suppl 2), S300-S303 (4 pages).

Port, Marc et al., "Efficiency, thermodynamic and kinetic stability of marketed gadolinium chelates and their possible clinical consequences: a critical review," *Biometals* (2008) 21:469-490 (22 pages).

Polasek, Miloslav et al., "Is Macrocycle a Synonym for Kinetic Inertness in Gd(III) Complexes? Effect of Coordinating and Noncoordinating Substituents on Inertness and Relaxivity of Gd(III) Chelates with DO3A-like Ligands," *Inorg. Chem.* 2013, 52, 4084-4096 (13 pages).

Ranganathan, Ramachandran S. et al., "Polymethylated DOTA Ligands. 1. Synthesis of Rigidified Ligands and Studies on the Effects of Alkyl Substitution on Acid-Base Properties and Conformational Mobility," *Inorg. Chem.* 2002, 41, 6846-6855 (10 pages).

Ranganathan, Ramachandran S. et al., "Polymethylated DOTA Ligands. 2. Synthesis of Rigidified Lanthanide Chelates and Studies on the Effect of Alkyl Substitution on Conformational Mobility and Relaxivity," *Inorg. Chem.* 2002, 41, 6856-6866 (11 pages).

Tircso, Gyula et al., "Analysis of the Conformational Behavior and Stability of the SAP and TSAP Isomers of Lanthanide(III) NB-DOTA-Type Chelates," *Inorg. Chem.* 2011, 50, 7966-7979 (14 pages).

Tóth, É et al., "Equilibrium and kinetic studies on complexes of 10-[2,3-dihydroxy-(1-hydroxymethyl)-propyl]-1,4,7,10-tetraazacyclododecane-1,4,7-triacetate," *Inorganica Chimica Acta* 249 (1996) 191-199 (9 pages).

Vander Elst, Luce et al., "Stereospecific binding of MRI contrast agents to human serum albumin: the case of Gd-(S)-EOB-DTPA (Eovist) and its (R) isomer," *J Biol Inorg Chem* (2001) 6:196-200 (5 pages).

Wahsner, Jessica et al., "Chemistry of MRI Contrast Agents: Current Challenges and New Frontiers," *Chem. Rev.* 2019, 119, 957-1057 (101 pages).

Webber, Benjamin C. et al., "Structural Analysis of Isomeric Europium(III) Chelates of NB-DOTMA," *Inorg. Chem.* 2012, 51, 8576-8582 (7 pages).

Webber, Benjamin C et al., "The confluence of structure and dynamics in lanthanide(III) chelates: how dynamics help define structure in solution," *Dalton Trans.*, 2014, 43, 251-258 (8 pages).

Webber, Benjamin C. et al., "Analysis of the Relaxometric Properties of Extremely Rapidly Exchanging $Gd^{3+}$ Chelates: Lessons from a Comparison of Four Isomeric Chelates," *Inorg. Chem.* 2020, 59, 9037-9046 (10 pages).

Woods, Mark, "Chiral gadolinium complexes as potential contrast agents," Durham theses, Durham University (1998) (253 pages).

Woods, Mark et al., "Correlation of Water Exchange Rate with Isomeric Composition in Diastereoisomeric Gadolinium Complexes of Tetra(carboxyethyl)dota and Related Macrocyclic Ligands," *J. Am. Chem. Soc.* 2000, 122, No. 40, 9781-9792 (12 pages).

Woods, Mark et al., "Towards the Rational Design of Magnetic Resonance Imaging Contrast Agents: Isolation of the Two Coordination Isomers of Lanthanide DOTA-Type Complexes," *Angew. Chem. Int. Ed.* 2003, 42, 5889-5892 (4 pages).

Woods, Mark et al., "Solution Dynamics and Stability of Lanthanide(III) (S)-2-(p-Nitrobenzyl)DOTA Complexes," *Inorg. Chem.* 2004, 43, No. 9, 2845-2851 (7 pages).

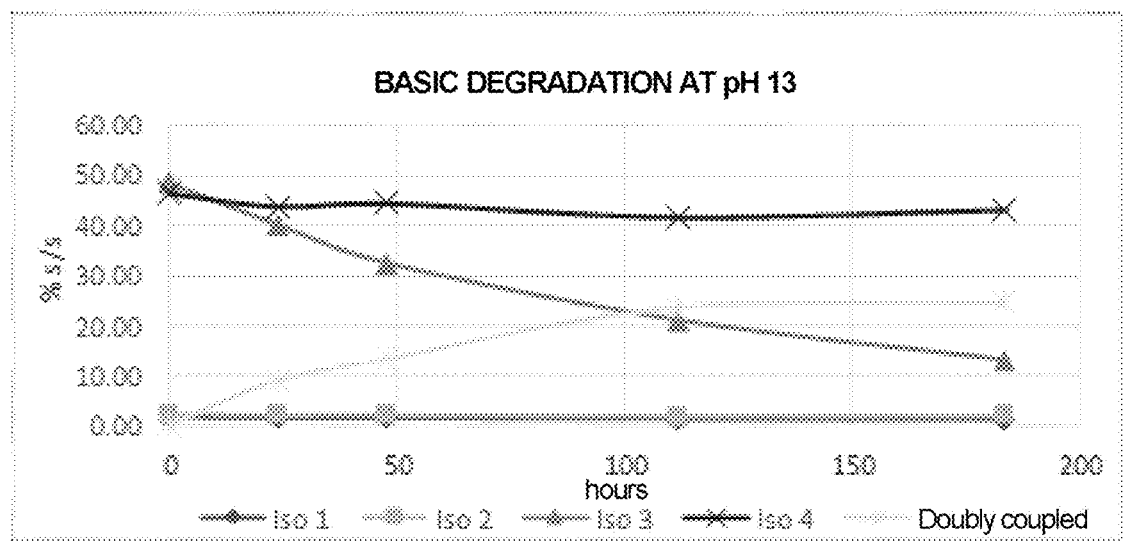

COMPLEX OF GADOLINIUM AND A CHELATING LIGAND DERIVED OF A DIASTEREOISOMERICALLY ENRICHED PCTA AND SYNTHESIS METHOD

CLAIM FOR PRIORITY

This is a continuation of application Ser. No. 17/423,589, filed Jul. 16, 2021, which is a National Stage Application under 35 U.S.C. § 371 of International Application No. PCT/EP2020/051142, filed Jan. 17, 2020, which claims the benefit to French Patent Application No. 1900433, filed Jan. 17, 2019, all of which are incorporated herein by reference in their entirety.

The present invention relates to a novel process for synthesizing a complex of gadolinium and of a PCTA-based chelating ligand, which makes it possible to obtain preferentially stereoisomers of said complex which have physicochemical properties that are most particularly advantageous for applications as contrast agent in the field of medical imaging, notably for magnetic resonance imaging. The present invention also relates to the diastereoisomerically enriched complex per se, and also to two synthetic intermediates, containing gadolinium or not.

Many contrast agents based on chelates of lanthanides (paramagnetic metal), in particular gadolinium (Gd), are known, for example described in U.S. Pat. No. 4,647,447. These products are often grouped under the term GBCA (gadolinium-based contrast agent). Several products are marketed, among which are macrocyclic chelates such as meglumine gadoterate based on DOTA (1,4,7,10-tetraazacyclododecane-N,N',N'',N'''-tetraacetic acid), gadobutrol based on DO3A-butrol, gadoteridol based on HPDO3A, and also linear chelates, notably based on DTPA (diethylenetriaminepentaacetic acid) or on DTPA-BMA (gadodiamide ligand).

Other products, some of which are under development, represent a new generation of GBCA. They are essentially complexes of macrocyclic chelates, such as bicyclopolyazamacrocyclocarboxylic acid complexes (EP 0 438 206) or PCTA derivatives (i.e. derivatives comprising a minima the 3,6,9,15-tetraazabicyclo[9,3,1]pentadeca-1(15),11,13-triene-3,6,9-triacetic acid chemical structure), as described in EP 1 931 673.

The complexes of PCTA-based chelating ligands described in EP 1 931 673 notably have the advantage of being relatively easy to synthesize chemically and, in addition, of having relaxivity superior to that of the other GBCAs (relaxivity $r_1$ which may be up to 11-12 mM$^{-1}$.s$^{-1}$ in water) currently on the market, this relaxivity corresponding to the efficiency of these products and thus to their contrasting power.

In the body, chelates (or complexes) of lanthanide—and notably of gadolinium—are in a state of chemical equilibrium (characterized by its thermodynamic constant $K_{therm}$), which may lead to an undesired release of said lanthanide (see equation 1 below):

Ch+Ln⇌Ch-Ln     (equation 1)

Complexation chemical equilibrium between the chelate or ligand (Ch) and the lanthanide (Ln) to give the complex Ch-Ln.

Since 2006, a pathology known as NSF (Nephrogenic Systemic Fibrosis or fibrogenic dermopathy), has been at least partly linked to the release of free gadolinium into the body.

This disease has alerted health authorities with regard to gadolinium-based contrast agents marketed for certain categories of patients.

Strategies were thus put into place to solve in an entirely safe manner the complex problem of patient tolerance and to limit, or even eliminate, the risk of undesired lanthanide release after administration. This problem is all the more difficult to solve since the administration of contrast agents is often repeated, whether during diagnostic examinations or for the adjustment of doses and the monitoring of the efficacy of a therapeutic treatment.

In addition, mention has been made since 2014 of a possible cerebral deposition of gadolinium after repeated administrations of gadolinium-based products, more particularly of linear gadolinium chelates, such a deposition having been sparingly or not at all reported with gadolinium macrocyclic chelates, such as Dotarem®. Consequently, various countries have decided either to withdraw the majority of the linear chelates from the market, or to drastically limit their indications for use, given their stability which is deemed insufficient.

A strategy for limiting the risk of lanthanide release into the body thus consists in opting for complexes which are distinguished by thermodynamic and/or kinetic stabilities that are as high as possible. The reason for this is that the more stable the complex, the more the amount of lanthanide released over time will be limited.

However, the complexes of PCTA-based chelating ligands comprising a structure of pyclene type described in EP 1 931 673, while having good kinetic stability, generally have a thermodynamic constant which is lower than that of complexes of the other cyclene-based macrocycles.

This is notably the case for the complex of formula (II) represented below:

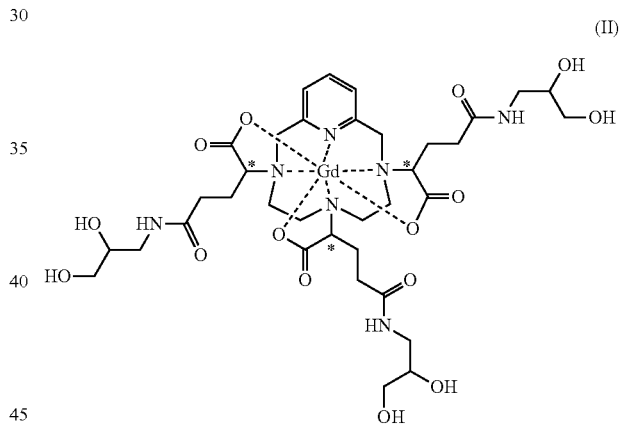

Indeed, as is notably described in WO 2014/174120, the thermodynamic equilibrium constant corresponding to the reaction for the formation of the complex of formula (II), also known as the stability constant, is $10^{14.9}$ (i.e. log $(K_{therm})$=14.9). For comparative purposes, the stability constant of the gadolinium complex of 1,4,7,10-tetraazacyclododecane-N,N',N'',N'''-tetraacetic acid (DOTA-Gd) is $10^{25.6}$ (i.e. log $(K_{therm})$=25.6).

It should be noted, however, that the complex of formula (II) corresponds to several stereoisomers, notably due to the presence of the three asymmetric carbon atoms located in the a position on the side chains of the complex, relative to the nitrogen atoms of the macrocycle onto which said side chains are grafted. These three asymmetric carbons are marked with an asterisk (*) in formula (II) represented above.

Thus, the synthesis of the complex of formula (II) as described in EP 1 931 673 results in the production of a mixture of stereoisomers.

The aminopropanediol groups of the side chains of the complex of formula (II) also include an asymmetric carbon. Thus, the complex of formula (II) comprises in total six asymmetric carbons, and thus exists in the form of 64 configurational stereoisomers. However, in the rest of the description, the only source of stereoisomerism considered for a given side chain will, for the sake of simplicity, be that corresponding to the asymmetric carbon bearing the carboxylate group, marked with an asterisk (*) in formula (II) represented above.

Since each of these three asymmetric carbons may be of R or S absolute configuration, the complex of formula (II) exists in the form of eight families of stereoisomers, referred to hereinbelow as II-RRR, II-SSS, II-RRS, II-SSR, II-RSS, II-SRR, II-RSR and II-SRS. More precisely, according to the usual nomenclature in stereochemistry, the complex of formula (II) exists in the form of eight families of diastereoisomers.

The use of the term "family" is justified in that each of these families includes several stereoisomers, notably due to the presence of an asymmetric carbon within the aminopropanediol group, as mentioned previously.

will be used without distinction, without stating that each corresponds to a family of stereoisomers.

The inventors have succeeded in separating and in identifying by high-performance liquid chromatography (HPLC) and by ultra-high-performance liquid chromatography (UHPLC) four unresolved peaks or groups of isomers of the complex of formula (II) obtained according to the process of the prior art, corresponding to four different elution peaks characterized by their retention time on the chromatogram, which will be referred to in the rest of the description as iso1, iso2, iso3 and iso4. By performing the process described in EP 1 931 673, the respective contents of the groups iso1, iso2, iso3 and iso4 in the mixture obtained are as follows: 20%, 20%, 40% and 20%.

They then discovered that these various groups of isomers had different physicochemical properties, and determined that the group of isomers known as iso4, which comprises a mixture of the isomers II-RRR and II-SSS of formulae (II-RRR) and (II-SSS) represented below, proves to be the most advantageous as contrast agent for medical imaging.

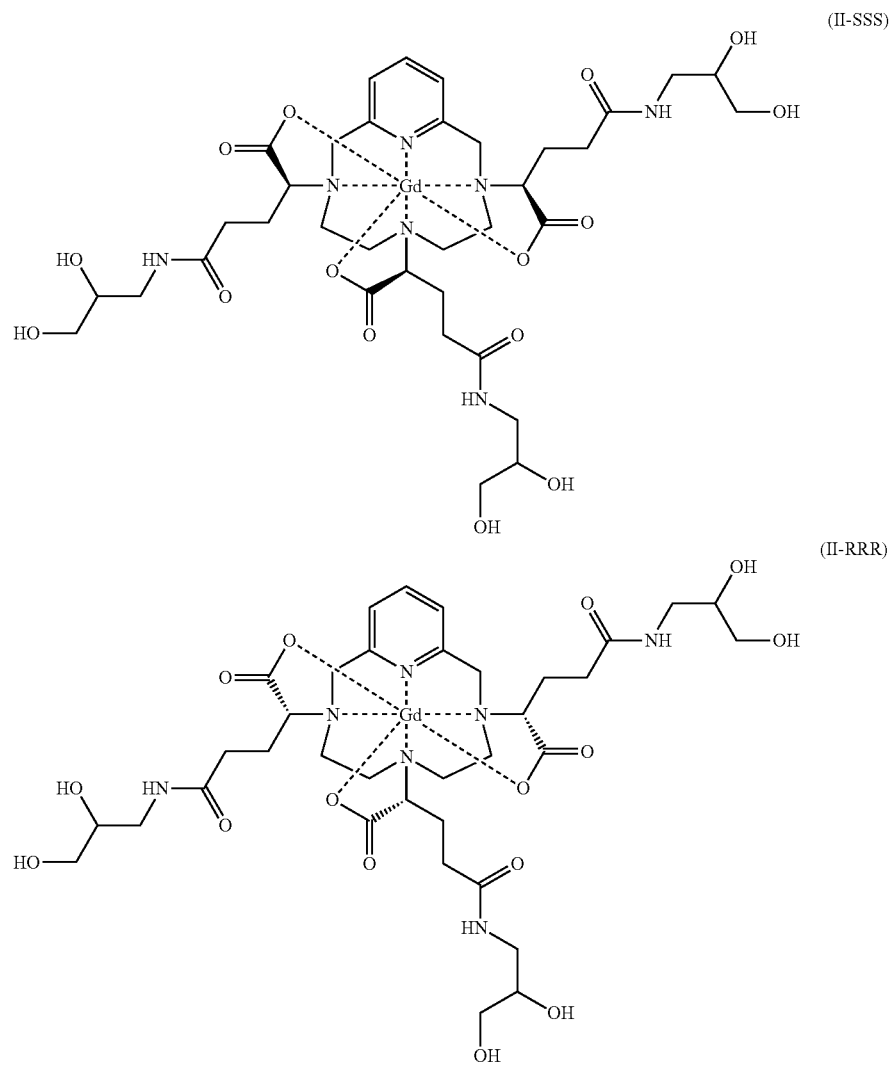

Nevertheless, since, in the rest of the description, the stereoisomerism associated with the asymmetric carbon of a given aminopropanediol group will not be considered, the terms isomers, stereoisomers or diastereoisomers II-RRR, II-SSS, II-RRS, II-SSR, II-RSS, II-SRR, II-RSR and II-SRS Indeed, iso4 is distinguished, surprisingly, by a thermodynamic stability that is markedly superior to that of the mixture of diastereoisomers in the form of which the complex of formula (II) is obtained by performing the process described in EP 1 931 673. Specifically, its equilibrium thermodynamic constant $K_{therm\ iso4}$ is equal to $10^{18.7}$ (i.e. log ($K_{therm\ iso4}$)=18.7) this value having been determined by performing the method described in Pierrard et al., *Contrast Media Mol. Imaging*, 2008, 3, 243-252 and Moreau et al., *Dalton Trans.*, 2007, 1611-1620.

Besides, iso4 is the group of isomers which has the best kinetic inertia (also known as kinetic stability) among the four groups isolated by the inventors. Specifically, the inventors evaluated the kinetic inertia of the four groups of isomers by studying their decomplexation kinetics in acidic aqueous solution (pH=1.2), at 37° C. The half-life time values ($T_{1/2}$) which were determined for each of the groups of isomers are indicated in table 1 below, the half-life time corresponding to the time after which 50% of the amount of complex initially present has been dissociated, according to the following decomplexation reaction (equation 2):

TABLE 1-continued decomplexation kinetics for the groups of isomers iso1 to iso4

| Groups of isomers | $T_{1/2}$ (pH 1.2-37° C.) |
|---|---|
| Iso3 | 8 days |
| Iso4 | 27 days |

For comparative purposes, gadobutrol or gadoterate, which are macrocyclic gadolinium complexes, respectively have a kinetic inertia of 18 hours and of 4 days under the

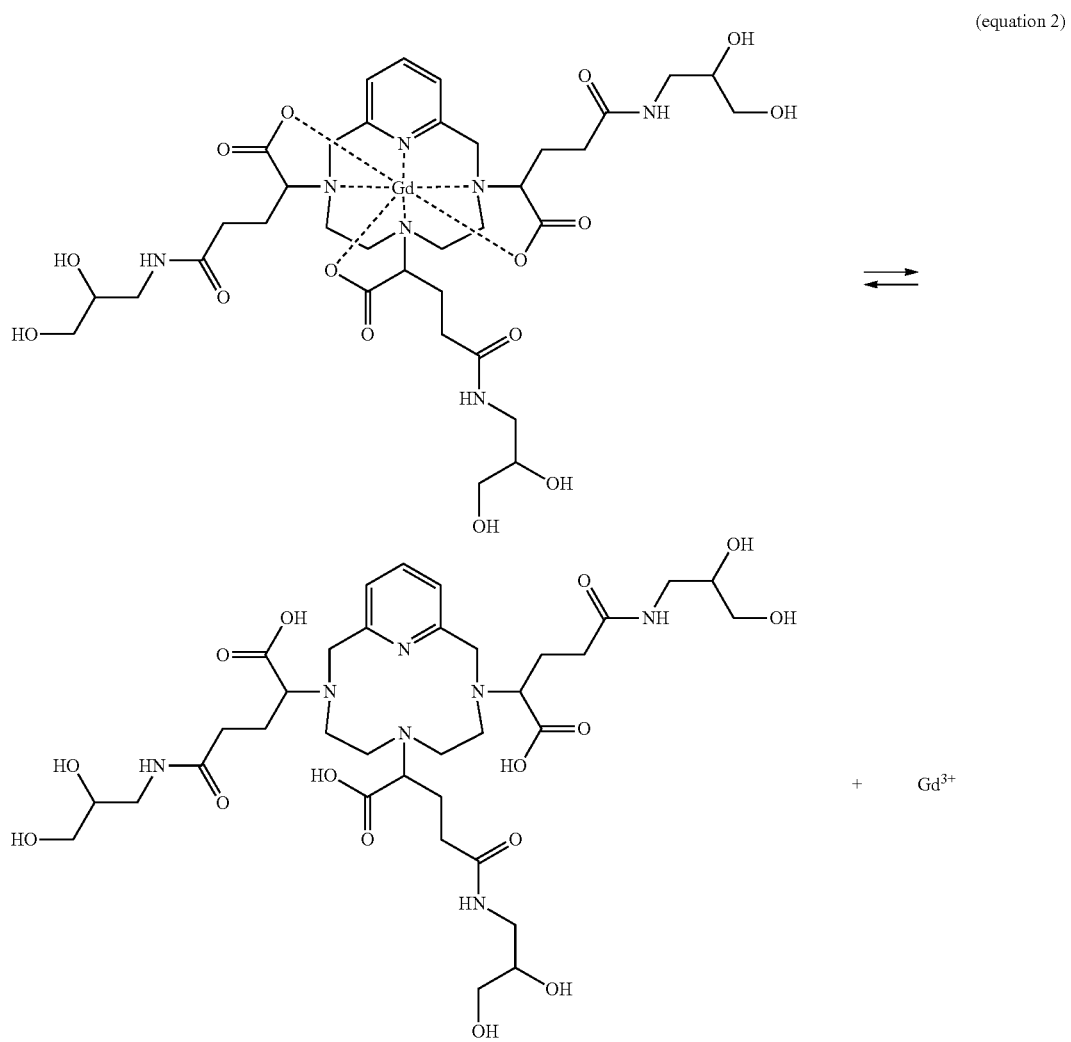

(equation 2)

+ $Gd^{3+}$

TABLE 1 decomplexation kinetics for the groups of isomers iso1 to iso4

| Groups of isomers | $T_{1/2}$ (pH 1.2-37° C.) |
|---|---|
| Iso1 | 18 hours |
| Iso2 | 6 hours | same conditions, whereas linear gadolinium complexes such as gadodiamide or gadopentetate dissociate instantaneously.

In addition, iso4 is chemically more stable than iso3, notably. The reason for this is that the amide functions of the complex of formula (II) are liable to be hydrolysed. The hydrolysis reaction of an amide function (equation 3) results in the formation of a dicoupled impurity, which is accompanied by the release of 3-amino-1,2-propanediol. The inventors studied the kinetics of the hydrolysis reaction of the complex of formula (II) in aqueous solution at pH 13 and observed that the amide functions of iso4 are more stable with respect to hydrolysis than those of iso3.

into the most stable stereoisomers, which, surprisingly, while being performed on the hexaacid intermediate com-

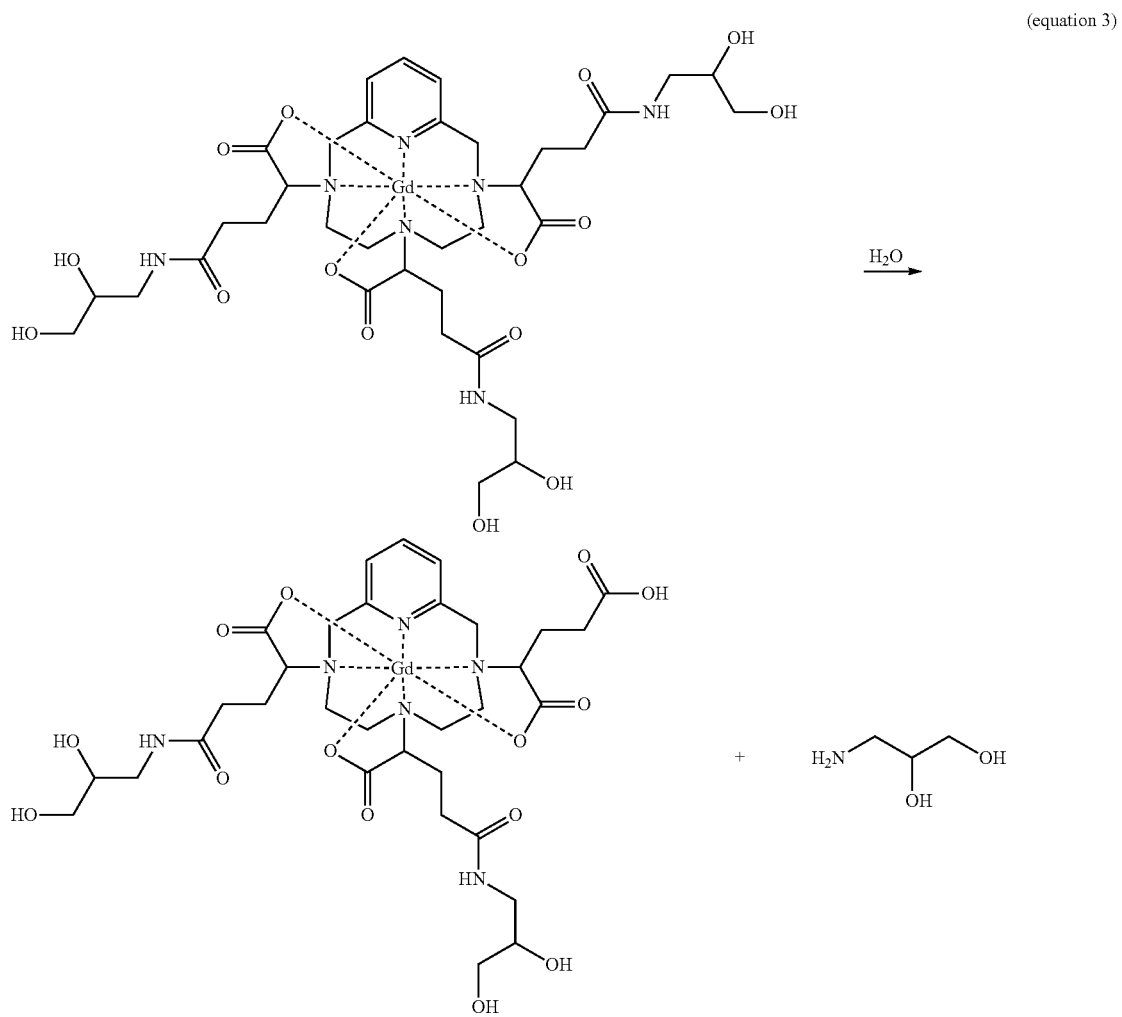

(equation 3)

As regards the relaxivity of the various groups of isomers, i.e. their efficiency as contrast agent, the measurements taken demonstrate a contrasting power that is relatively equivalent for the groups iso1, iso2 and iso4, and reduced efficiency for iso3 (see table 2).

TABLE 2 relaxivity of the groups of isomers iso1 to iso4 at 37° C.

| Groups of isomers | r1 20 MHz ($mM^{-1} \cdot s^{-1}$) | r1 60 MHz ($mm^{-1} \cdot s^{-1}$) |
| --- | --- | --- |
| Iso1 | 12.6 | 12.5 |
| Iso2 | 13.3 | 12.9 |
| Iso3 | 8.0 | 8.1 |
| Iso4 | 12.9 | 13.0 |

The inventors have succeeded in developing a novel process for preparing the complex of formula (II), making it possible to obtain preferentially the diastereoisomers II-RRR and II-SSS of said complex, which have particularly advantageous physicochemical properties. The process according to the invention comprises a step of isomeric enrichment, by conversion of the least stable stereoisomers plex and not on the final complex, makes it possible to obtain very predominantly the most stable isomers of the complex of formula (II).

The implementation of a process which makes it possible to obtain predominantly the diastereoisomers of interest is unquestionably advantageous when compared with the alternative consisting in preparing the mixture of stereoisomers, then subsequently attempting to separate the diastereoisomers according to the usual techniques and thus to isolate the isomers of interest. Indeed, besides the fact that it is easier to perform a process not involving a step of separation of diastereoisomers on an industrial scale, the absence of separation firstly affords considerable time-saving and secondly makes it possible to improve the overall yield of the process, by limiting as much as possible the production of the undesired diastereoisomers which would ultimately be discarded. Moreover, the usual separation techniques generally involve an abundant use of solvents, which, beyond the financial cost, is not desirable for environmental reasons. Furthermore, chromatography on silica is in particular to be avoided, given the health risks inherent in professional exposure to silica, which is classified as carcinogenic to humans (group 1) by the International Agency for Research on Cancer.

As indicated previously, the process for preparing the complex of formula (II) developed by the inventors is based on a step of isomeric enrichment of the intermediate hexaacid gadolinium complex of formula (I) represented below:

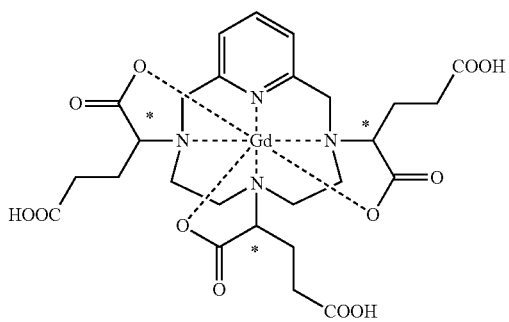

(I)

The complex of formula (I) corresponds to several stereoisomers, due to the presence of the three asymmetric carbon atoms located in the a position on the side chains of the complex, relative to the nitrogen atoms of the macrocycle onto which said side chains are grafted. These three asymmetric carbons are marked with an asterisk (*) in formula (I) represented above.

Since each of the three asymmetric carbons bearing a carboxylate function may be of R or S absolute configuration, the complex of formula (I) exists in the form of eight stereoisomers, referred to hereinbelow as I-RRR, I-SSS, I-RRS, I-SSR, I-RSS, I-SRR, I-RSR and I-SRS. More precisely, according to the usual nomenclature in stereochemistry, the complex of formula (I) exists in the form of four pairs of enantiomers, which are mutual diastereoisomers.

The inventors have succeeded in separating and in identifying by high-performance liquid chromatography (HPLC) and by ultra-high-performance liquid chromatography (UHPLC) four unresolved peaks or groups of isomers of the complex of formula (I) obtained according to the process described in EP 1 931 673, corresponding to four different elution peaks characterized by their retention time on the chromatogram, which will be referred to in the rest of the description as isoA, isoB, isoC and isoD.

IsoD crystallizes from water. X-ray diffraction analysis enabled the inventors to determine the crystal structure of this group of isomers, and thus to discover that it comprises the diastereoisomers I-RRR and I-SSS of the complex of formula (I), of formulae (I-RRR) and (I-SSS) represented below.

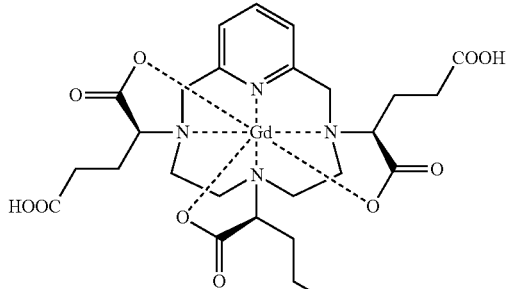

(I-SSS)

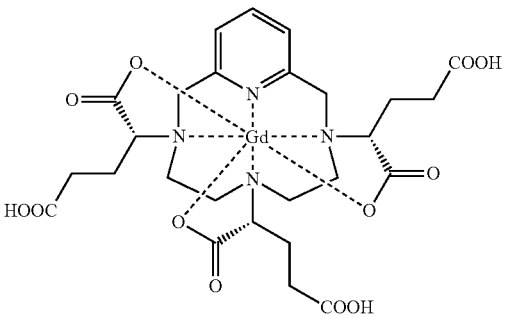

(I-RRR)

It should be noted that the diastereoisomers I-RRR and I-SSS of the complex of formula (I) are enantiomers of each other.

The isomeric enrichment step of the process of the invention aims at enriching the intermediate hexaacid gadolinium complex of formula (I) in isoD.

The synthesis of the complex of formula (II) notably involves conversion of the carboxylic acid functions of the intermediate hexaacid complex of formula (I) into amide functions. This amidation reaction does not modify the absolute configuration of the three asymmetric carbon atoms of the complex of formula (I).

Thus, when the amidation reaction is performed on the hexaacid complex of formula (I) enriched in isoD obtained previously, it makes it possible to obtain the complex of formula (II) enriched in iso4.

Hexaacid Gadolinium Complex of Formula (I)

The present invention thus relates firstly to a hexaacid gadolinium complex of formula (I):

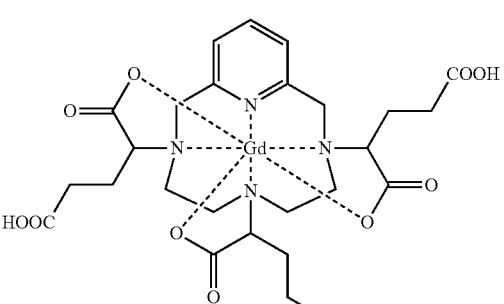

(I)

constituted of at least 80% of a diastereoisomeric excess comprising a mixture of isomers I-RRR and I-SSS of formulae:

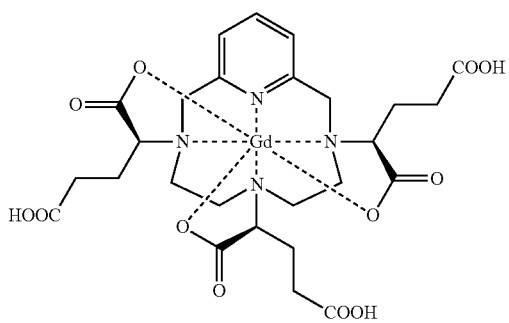

(I-SSS)

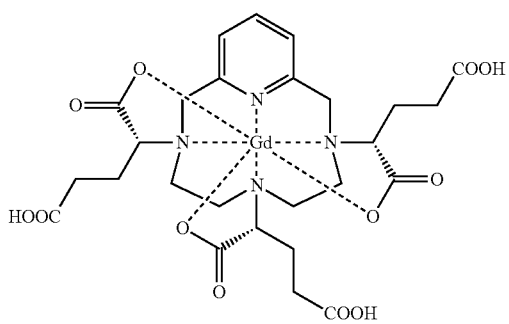

(I-RRR)

In the context of the present invention, the term "diastereoisomeric excess" is intended to denote, as regards the hexaacid gadolinium complex of formula (I), the fact that said complex is predominantly present in the form of an isomer or group of isomers chosen from the diastereoisomers I-RRR, I-SSS, I-RRS, I-SSR, I-RSS, I-SRR, I-RSR and I-SRS. Said diastereoisomeric excess is expressed as a percentage and corresponds to the amount represented by the predominant isomer or group of isomers relative to the total amount of the hexaacid gadolinium complex of formula (I). It is understood that this percentage may be on either a molar or mass basis, since isomers have, by definition, the same molar mass.

In one particular embodiment, the complex of formula (I) according to the invention has at least 85%, notably at least 90%, in particular at least 95%, preferably at least 97%, advantageously at least 98%, more advantageously at least 99% of the diastereoisomeric excess comprising the mixture of isomers I-RRR and I-SSS.

Preferably, said diastereoisomeric excess is constituted of at least 70%, notably of at least 80%, advantageously of at least 90%, preferably of at least 95% of the mixture of isomers I-RRR and I-SSS.

Advantageously, said diastereoisomeric excess consists of the mixture of isomers I-RRR and I-SSS.

The term "mixture of isomers I-RRR and I-SSS" also covers, by extension, the case where only one of the isomers, whether it be I-RRR or I-SSS, is present. However, the term "mixture of isomers I-RRR and I-SSS" preferentially denotes all the cases in which each of the isomers I-RRR and I-SSS is present in a variable but non-zero amount.

In a preferred embodiment, the isomers I-RRR and I-SSS are present in said mixture in a ratio of between 65/35 and 35/65, notably between 60/40 and 40/60, in particular between 55/45 and 45/55. Advantageously, the mixture of isomers I-RRR/I-SSS is a racemic (50/50) mixture.

More particularly, the diastereoisomeric excess as defined previously corresponds to peak 4 in the HPLC plot (i.e. the fourth peak in the order of elution and corresponding to isoD), characterized by a retention time of between 33.9 and 37.5 minutes, typically of about 35.7 minutes, said plot being obtained using the HPLC method described below.

For the purposes of the present invention, the term "HPLC plot" means the profile of the concentrations measured by the detector after passage and separation of a mixture of compounds (in this instance of isomers of a compound) on a stationary phase as a function of time for a given composition and a given flow rate of eluent. The HPLC plot is constituted of various peaks or unresolved peaks characteristic of the compound or of the mixture of compounds analysed.

HPLC Method:

Waters Symmetry® C18–250×4.6 mm–5 μm column.

It is a reverse-phase HPLC column containing spherical silica particles with C18 (octadecyl) grafting, and the silanols of which have been treated with capping agents (end-capped). It is also characterized by a length of 250 mm, an inside diameter of 4.6 mm, a particle size of 5 μm, a porosity of 100 Å and a carbon content of 19%.

Preferentially, the stationary phase used should be compatible with the aqueous mobile phases.

analytical conditions:

| Sample | Aqueous solution of the complex of formula (I) at 10 mg/mL |
| --- | --- |
| Column temperature | 25° C. |
| Sample temperature | Room temperature (20-25° C.) |
| Flow rate | 1.0 mL/min |
| Injection volume | 20 μL |
| UV detection | 200 nm | mobile phase gradient (by volume):

| Time (min) | % acetonitrile (100%) | % $H_2SO_4$ (aqueous solution at 0.1% v/v) |
| --- | --- | --- |
| 0 | 1 | 99 |
| 10 | 5 | 95 |
| 40 | 10 | 90 |

Complex of Formula (II)

The present invention relates secondly to a complex of formula (II):

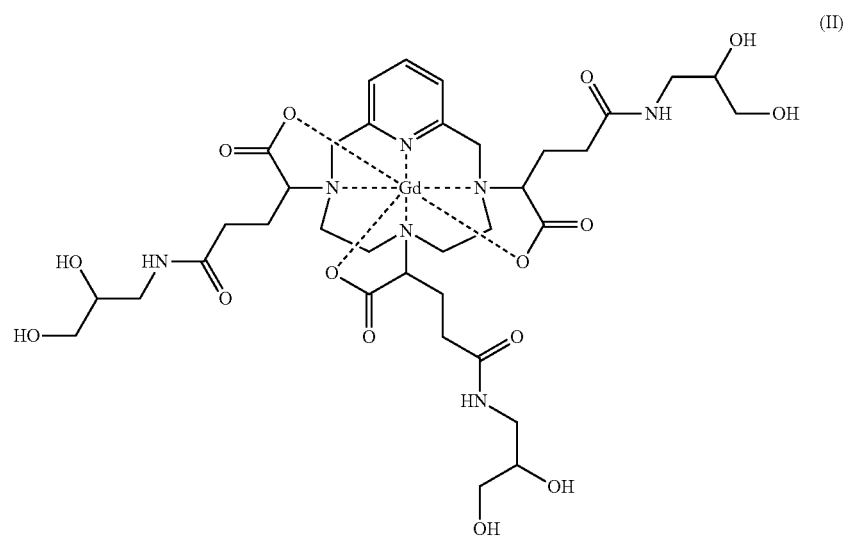
constituted of at least 80% of a diastereoisomeric excess comprising a mixture of isomers II-RRR and II-SSS of formulae:
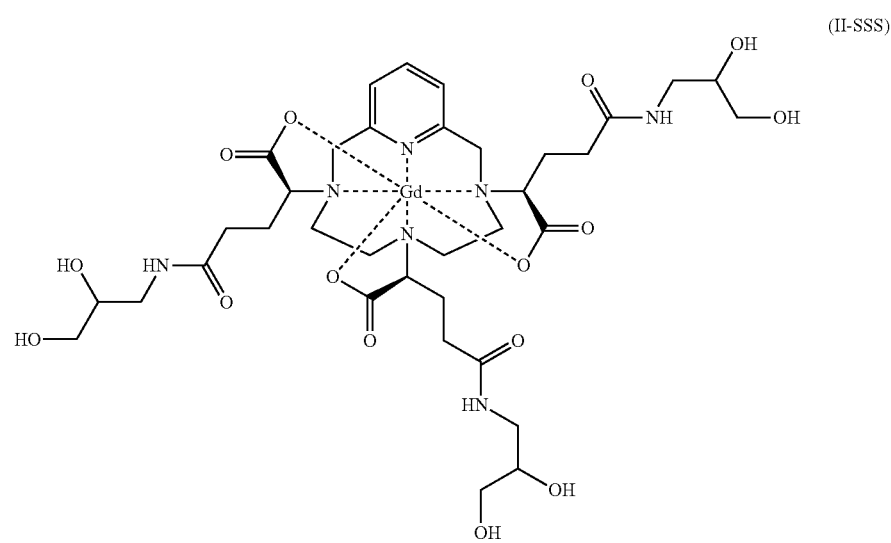

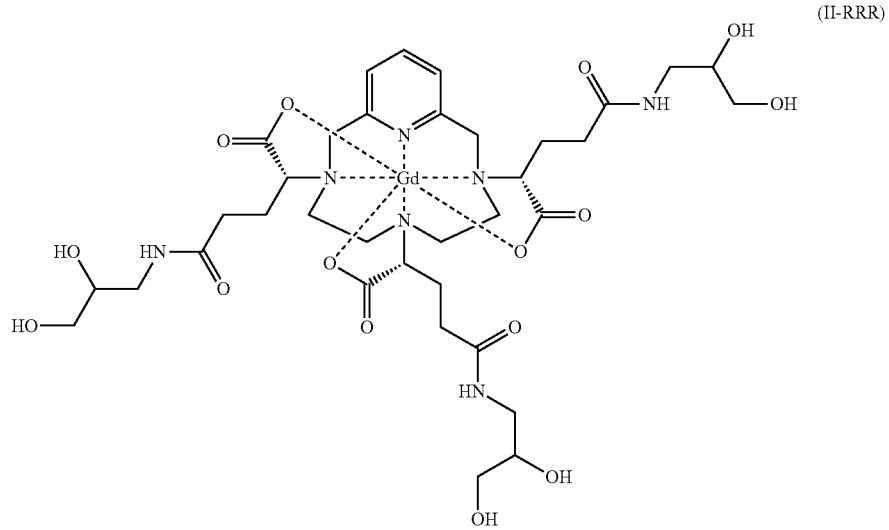

(II-RRR)

In the context of the present invention, the term "diastereoisomeric excess" is intended to denote, as regards the complex of formula (II), the fact that said complex is predominantly present in the form of an isomer or group of isomers chosen from the diastereoisomers II-RRR, II-SSS, II-RRS, II-SSR, II-RSS, II-SRR, II-RSR and II-SRS. Said diastereoisomeric excess is expressed as a percentage and corresponds to the amount represented by the predominant isomer or group of isomers relative to the total amount of the complex of formula (II). It is understood that this percentage may be on either a molar or mass basis, since isomers have, by definition, the same molar mass.

In one particular embodiment, the complex of formula (II) according to the invention has at least 85%, notably at least 90%, in particular at least 92%, preferably at least 94%, advantageously at least 97%, more advantageously at least 99% of the diastereoisomeric excess comprising the mixture of isomers II-RRR and II-SSS.

Preferably, said diastereoisomeric excess is constituted of at least 70%, notably of at least 80%, advantageously of at least 90%, preferably of at least 95% of the mixture of isomers II-RRR and II-SSS.

Advantageously, said diastereoisomeric excess consists of the mixture of isomers II-RRR and II-SSS.

The term "mixture of isomers II-RRR and II-SSS" also covers, by extension, the case where only one of the isomers, whether it be II-RRR or II-SSS, is present. However, the term "mixture of isomers II-RRR and II-SSS" preferentially denotes all the cases in which each of the isomers II-RRR and II-SSS is present in a variable but non-zero amount.

In a preferred embodiment, the isomers II-RRR and II-SSS are present in said mixture in a ratio of between 65/35 and 35/65, notably between 60/40 and 40/60, in particular between 55/45 and 45/55. Advantageously, the isomers II-RRR and II-SSS are present in the mixture in a 50/50 ratio.

More particularly, the diastereoisomeric excess as defined previously corresponds to peak 4 in the UHPLC plot (i.e. the fourth unresolved peak of isomers in the order of elution and corresponding to iso4), characterized by a retention time of between 6.0 and 6.6 minutes, typically of about 6.3 minutes, said plot being obtained using the UHPLC method described below.

For the purposes of the present invention, the term "UHPLC plot" means the profile of the concentrations measured by the detector after passage and separation of a mixture of compounds (in this instance of isomers of a compound) on a stationary phase as a function of time for a given composition and a given flow rate of eluent. The UHPLC plot is constituted of various peaks or unresolved peaks characteristic of the compound or of the mixture of compounds analysed.

UHPLC Method:

Waters Cortecs® UPLC T3 150×2.1 mm-1.6 μm column.

It is a reverse-phase UPLC column containing spherical particles constituted of a core, which is preferentially very hard, made of silica, surrounded by a porous silica with trifunctional C18 (octadecyl) grafting, and the silanols of which have been treated with capping agents (end-capped). It is also characterized by a length of 150 mm, an inside diameter of 2.1 mm, a particle size of 1.6 μm, a porosity of 120 Å and a carbon content of 4.7%.

Preferentially, the stationary phase used should be compatible with the aqueous mobile phases.

analytical conditions:

| Sample | Aqueous solution of the complex of formula (II) at 2.0 mg/mL |
| --- | --- |
| Column temperature | 40° C. |
| Sample temperature | Room temperature (20-25° C.) |
| Flow rate | 0.3 mL/min |
| Injection volume | 1 μL |
| UV detection | 200 nm | mobile phase gradient (% v/v):

| Time (min) | Acetonitrile (100%) | $H_2SO_4$ (aqueous solution at 0.0005% v/v) |
| --- | --- | --- |
| 0 | 1 | 99 |
| 3 | 5 | 95 |
| 12 | 10 | 90 |

In a preferred embodiment, the complex of formula (II) according to the invention is obtained by amidation starting with the complex of formula (I) according to the invention as defined above and 3-amino-1,2-propanediol, in racemic or enantiomerically pure form, preferably in racemic form.

For the purposes of the present invention, the term "amidation" means the reaction for conversion of a carboxylic acid function into an amide function by reaction with an amine function.

Such a reaction may notably be performed after activation of the carboxylic acid functions, as is detailed in the continuation of the description.

Process for Preparing the Complex of Formula (II)

The present invention also relates to a process for preparing the complex of formula (II), comprising the following successive steps:

a) Complexation of the hexaacid of formula (III) below:

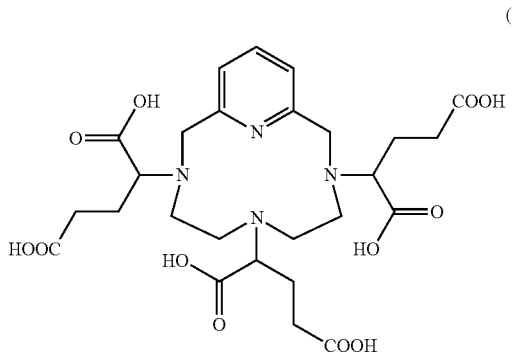

(III)

with gadolinium to obtain the hexaacid gadolinium complex of formula (I) as defined previously, b) Isomerization by heating the hexaacid gadolinium complex of formula (I) in an aqueous solution at a pH of between 2 and 4, to obtain a diastereoisomerically enriched complex constituted of at least 80% of a diastereoisomeric excess comprising a mixture of the isomers I-RRR and I-SSS of said hexaacid gadolinium complex of formula (I), and c) Formation, starting with the diastereoisomerically enriched complex obtained in step b), of the complex of formula (II), by reaction with 3-amino-1,2-propanediol.

In the present description, unless otherwise mentioned, the terms "Gd", "gadolinium" and "Gd$^{3+}$" are used without distinction to denote the Gd$^{3+}$ ion. By extension, it may also be a source of free gadolinium, such as gadolinium chloride (GdCl$_3$) or gadolinium oxide (Gd$_2$O$_3$).

In the present invention, the term "free Gd" denotes the non-complexed forms of gadolinium, which are preferably available for complexation. It is typically the Gd$^{3+}$ ion dissolved in water. By extension, it may also be a source of free gadolinium, such as gadolinium chloride (GdCl$_3$) or gadolinium oxide.

Step a)

In this step, a complexation reaction takes place between the hexaacid of formula (III) and gadolinium, which makes it possible to obtain the hexaacid gadolinium complex of formula (I) as defined previously.

According to a particular embodiment, step a) comprises the reaction between the hexaacid of formula (III) and a source of free Gd in water.

In a preferred embodiment, the source of free Gd is GdCl$_3$ or Gd$_2$O$_3$, preferably Gd$_2$O$_3$.

Preferably, the reagents used in step a), i.e. the source of gadolinium (typically gadolinium oxide), the hexaacid of formula (III) and water, are as pure as possible, notably as regards the metal impurities.

Thus, the source of gadolinium will advantageously be gadolinium oxide, preferably with a purity of greater than 99.99% and even more preferably greater than 99.999%.

The water used in the process preferably comprises less than 50 ppm of calcium, more preferably less than 20 ppm and most preferably less than 15 ppm of calcium. Generally, the water used in the process is deionized water, water for injection (injection-grade water) or purified water.

Advantageously, the amounts of the reagents (the hexaacid of formula (III) and gadolinium) used in this step a) correspond to, or are close to, stoichiometric proportions, as dictated by the balance equation of the complexation reaction which takes place during this step.

The term "close to stoichiometric proportions" means that the difference between the molar proportions in which the reagents are introduced and the stoichiometric proportions is less than 15%, notably less than 10%, preferably less than 8%.

Gadolinium may notably be introduced in slight excess relative to the stoichiometric proportions. The ratio of the amount of material introduced as gadolinium to the amount of material introduced as hexaacid of formula (III) is then greater than 1, but typically less than 1.15, notably less than 1.10, advantageously less than 1.08. In other words, the amount of gadolinium introduced is greater than 1 equivalent (eq.), but typically less than 1.15 eq., notably less than 1.10 eq., advantageously less than 1.08 eq., relative to the amount of hexaacid of formula (III) introduced, which itself corresponds to 1 equivalent. In the preferred embodiment in which the source of free gadolinium is Gd$_2$O$_3$, the amount of Gd$_2$O$_3$ introduced is then typically greater than 0.5 eq., but less than 0.575 eq., notably less than 0.55 eq., advantageously less than 0.54 eq., relative to the amount of hexaacid of formula (III) introduced (1 eq.).

According to a particular embodiment, step a) comprises the following successive steps:

a1) Preparation of an aqueous solution of hexaacid of formula (III), and a2) Addition, to the aqueous solution obtained in step a1), of a source of free gadolinium.

In this embodiment, the content of hexaacid of formula (III) in the aqueous solution prepared in step a1) is typically between 10% and 60%, notably between 15% and 45%, preferably between 20% and 35%, advantageously between 25% and 35% and even more advantageously between 25% and 30% by weight relative to the total weight of the aqueous solution.

Preferentially, steps a) and b) are performed according to a one-pot embodiment, i.e. in the same reactor and without an intermediate step of isolation or purification.

Thus, in this preferred embodiment, the hexaacid gadolinium complex of formula (I) formed in step a) is directly subjected to the isomerization step b) without being isolated or purified, and in the same reactor as that used for step a).

Step b)

The hexaacid gadolinium complex of formula (I) formed by the complexation reaction between the hexaacid of formula (III) and gadolinium in step a) is initially obtained in the form of a mixture of diastereoisomers.

Step b) aims at enriching the mixture of diastereoisomers in the isomers I-RRR and I-SSS, to obtain the diastereoisomerically enriched hexaacid gadolinium complex of formula (I) constituted of at least 85%, notably of at least 90%, in particular of at least 95%, preferably of at least 97%, advantageously of at least 98%, more advantageously of at least 99% of the diastereoisomeric excess comprising the mixture of the isomers I-RRR and I-SSS.

Preferably, said diastereoisomeric excess is constituted of at least 70%, notably of at least 80%, advantageously of at least 90%, preferably of at least 95% of the mixture of isomers I-RRR and I-SSS.

Advantageously, said diastereoisomeric excess consists of the mixture of isomers I-RRR and I-SSS.

The inventors have in fact discovered that factors such as the pH and the temperature of the solution of hexaacid gadolinium complex of formula (I) obtained on conclusion of step a) have an influence on the ratio in which the various isomers of the complex of formula (I) are present in the mixture of diastereoisomers. Over time, the mixture tends to become enriched in a group of isomers comprising the isomers which are, surprisingly, the most thermodynamically stable but also the most chemically stable, in this instance the isomers I-RRR and I-SSS.

The term "mixture of isomers I-RRR and I-SSS" also covers, by extension, the case where only one of the isomers, whether it be I-RRR or I-SSS, is present. However, the term "mixture of isomers I-RRR and I-SSS" preferentially denotes all the cases in which each of the isomers I-RRR and I-SSS is present in a variable but non-zero amount.

In a preferred embodiment, the isomers I-RRR and I-SSS are present in said mixture in a ratio of between 65/35 and 35/65, notably between 60/40 and 40/60, in particular between 55/45 and 45/55. Advantageously, the mixture of isomers I-RRR/I-SSS is a racemic (50/50) mixture.

Step b) of isomerization of the hexaacid gadolinium complex of formula (I) in an aqueous solution is typically performed at a pH of between 2 and 4, notably between 2 and 3, advantageously between 2.2 and 2.8.

The pH is preferentially adjusted with an acid, preferably an inorganic acid, such as hydrochloric acid, hydrobromic acid, sulfuric acid, nitric acid or phosphoric acid, for example with hydrochloric acid.

It is entirely surprising that, under such pH conditions, enrichment of the mixture in particular isomers, in this instance the isomers I-RRR and I-SSS, takes place, since it is known in the art that gadolinium chelates are characterized by low kinetic inertia in acidic medium. Indeed, the higher the concentration of $H^+$ ions in the medium, the greater the probability that a proton is transferred onto one of the donor atoms of the ligand, thus bringing about dissociation of the complex. Consequently, a person skilled in the art would have expected that placing the hexaacid gadolinium complex of formula (I) in an aqueous solution at a pH of between 2 and 4 would bring about dissociation of said complex, rather than its isomerization into I-RRR and I-SSS.

It should be noted that the pH range recommended by EP 1 931 673 for the complexation of the hexaacid of formula (III), namely 5.0-6.5, does not make it possible to obtain the complex of formula (I) enriched in its isomers I-RRR and I-SSS.

Step b) is typically performed at a temperature of between 80° C. and 130° C., notably between 90° C. and 125° C., preferably between 98° C. and 122° C., advantageously between 100° C. and 120° C., typically for a time of between 10 hours and 72 hours, notably between 10 hours and 60 hours, advantageously between 12 hours and 48 hours.

Contrary to all expectations, such temperature conditions, which, combined with the abovementioned pH conditions, should favour the instability of the gadolinium chelate, do not result in its decomplexation or in the formation of any other impurity, but in its isomerization into I-RRR and I-SSS.

In one particular embodiment, the aqueous solution of step b) comprises acetic acid. Step b) is then advantageously performed at a temperature of between 100° C. and 120° C., notably between 110° C. and 118° C., typically for a time of between 12 hours and 48 hours, notably between 20 hours and 30 hours, in particular between 24 hours and 26 hours.

The acetic acid is preferably added before the heating of the solution of hexaacid gadolinium complex of formula (I) obtained in step a) in an amount such that the acetic acid content is between 25% and 75%, notably between 40% and 50% by mass relative to the mass of hexaacid of formula (III) used in step a).

When the aqueous solution is heated to a temperature advantageously between 100° C. and 120° C., typically between 110° C. and 118° C., acetic acid is added gradually as the water evaporates, so as to maintain a constant volume of solution.

According to a preferred embodiment, on conclusion of step b), the diastereoisomerically enriched complex is isolated by crystallization, preferably by crystallization by seeding.

In this embodiment, step b) comprises the following successive steps:

b1) Isomerization by heating the hexaacid gadolinium complex of formula (I) in an aqueous solution at a pH of between 2 and 4 to obtain a diastereoisomerically enriched complex constituted of at least 80% of the diastereoisomeric excess comprising the mixture of the isomers I-RRR and I-SSS of said hexaacid gadolinium complex of formula (I), and b2) Isolation by crystallization of said diastereoisomerically enriched complex, preferably by crystallization by seeding.

The crystallization step b2) aims firstly at removing any impurities present in the aqueous solution, which may result from previous steps, so as to obtain a decolourized product of higher purity, in the form of crystals, and secondly at continuing the diastereoisomeric enrichment of the hexaacid gadolinium complex of formula (I), so as to obtain a diastereoisomeric excess comprising the mixture of the isomers I-RRR and I-SSS of said complex which is higher than that obtained on conclusion of step b1).

Indeed, the isomers I-RRR and I-SSS of the hexaacid complex of formula (I) crystallize from water. On the other hand, the hexaacid gadolinium complex of formula (I) not enriched in said isomers does not crystallize.

The fact that the isomers I-RRR and I-SSS, in which the complex tends to become enriched in the course of step b) (and, contrary to all expectations, in the light of the conditions under which it is performed), are the only isomers of the complex to crystallize from water is an entirely unexpected result. The isomerization and crystallization thus contribute synergistically towards the enrichment in isomers I-RRR and I-SSS and consequently towards the overall efficiency of the process according to the invention.

Moreover, it should be noted that crystallization in water of the isomers of interest of the hexaacid gadolinium complex of formula (I) makes it possible to avoid an addition of solvent as described in Example 7 of EP 1 931 673, which involves a step of precipitation from ethanol of the trisodium salt of said complex.

Step b2) is advantageously performed at a temperature of between 10° C. and 70° C., notably between 30° C. and 65° C., in particular between 35° C. and 60° C.

According to one variant, after lowering the temperature of the aqueous solution, so that it is within the ranges indicated above, the crystallization process is induced by seeding. "Crystallization by seeding", also known as "crystallization by priming", comprises the introduction into the reactor in which the crystallization is performed (also known as the crystallization vessel) of a known amount of crystals, known as "seed" or "primer". This makes it possible to reduce the crystallization time. Crystallization by seeding is well known to those skilled in the art. In the process according to the invention, seeding using a primer, in the present instance crystals of diastereoisomerically enriched hexaacid gadolinium complex of formula (I) added to the aqueous solution of the diastereoisomerically enriched complex whose temperature has been lowered beforehand, makes it possible to obtain nucleation, and thus to initiate the crystallization. The duration of the crystallization by seeding is advantageously between 2 hours and 20 hours and preferably between 6 hours and 18 hours; typically, it is 16 hours.

The crystals of diastereoisomerically enriched hexaacid gadolinium complex of formula (I) are then typically isolated by filtration and drying, by means of any technique well known to those skilled in the art.

Advantageously, the degree of purity of the diastereoisomerically enriched hexaacid gadolinium complex of formula (I) isolated on conclusion of step b2) is greater than 95%, notably greater than 98%, advantageously greater than 99%, said degree of purity being expressed as a mass percentage of the complex of formula (I) relative to the total mass obtained on conclusion of step b2).

In a particular embodiment, the diastereoisomerically enriched complex from step b) isolated by crystallization is again purified by recrystallization, to obtain a diastereoisomerically enriched and purified complex.

In this embodiment, step b) comprises, besides the successive steps b1) and b2) described previously, a step b3) of purification by recrystallization of the isolated diastereoisomerically enriched hexaacid gadolinium complex of formula (I).

The recrystallization step b3) aims, like the crystallization step b2), firstly at obtaining a product of higher purity, and secondly at continuing the diastereoisomeric enrichment of the hexaacid gadolinium complex of formula (I), so as to obtain a diastereoisomeric excess comprising the mixture of the isomers I-RRR and I-SSS of said complex which is higher than that obtained on conclusion of step b2).

Step b3) typically comprises the following successive substeps:
suspension of the diastereoisomerically enriched hexaacid gadolinium complex of formula (I) isolated in step b2) in aqueous solution, preferably in water,
dissolution of said complex by heating to a temperature advantageously between 80° C. and 120° C., for example to 100° C.,
recrystallization, preferably by seeding, at a temperature advantageously between 10° C. and 90° C., notably between 20° C. and 87° C., in particular between 55° C. and 85° C., typically for a time of between 2 hours and 20 hours, notably between 6 hours and 18 hours, and
isolation of the crystals of diastereoisomerically enriched and purified hexaacid gadolinium complex of formula (I), for example by filtration and drying.

The degree of purity of the purified diastereoisomerically enriched hexaacid gadolinium complex of formula (I) isolated on conclusion of step b3) is typically greater than 98%, notably greater than 99%, advantageously greater than 99.5%, said degree of purity being expressed as a mass percentage of the complex of formula (I) relative to the total mass obtained on conclusion of step b2).

In another embodiment, the diastereoisomerically enriched complex from step b) is further enriched by selective decomplexation of the diastereoisomers of the complex of formula (I) other than the diastereoisomers I-RRR and I-SSS, i.e. by selective decomplexation of the diastereoisomers I-RSS, I-SRR, I-RSR, I-SRS, I-RRS and I-SSR.

In this embodiment, step b) comprises, besides the successive steps b1) and b2) described previously, a step b4) of selective decomplexation of the diastereoisomers of the complex of formula (I) other than the diastereoisomers I-RRR and I-SSS. In this variant, step b) may also comprise step b3) described previously, said step b3) being performed between steps b2) and b4), or after b4).

The selective decomplexation step b4) is directed towards continuing the diastereoisomeric enrichment of the hexaacid gadolinium complex of formula (I), so as to obtain a diastereoisomeric excess comprising the mixture of the isomers I-RRR and I-SSS of said complex which is higher than that obtained on conclusion of step b2) or on conclusion of step b3), when said step is performed prior to step b4).

Step b4) typically comprises the following successive substeps:
suspension of the diastereoisomerically enriched hexaacid gadolinium complex of formula (I) isolated in step b2) or in step b3) in water,
addition of a base, for example sodium hydroxide,
heating to a temperature advantageously between 30° C. and 60° C., notably between 35° C. and 55° C., for example at 40° C., typically for a time of between 2 hours and 20 hours, notably between 10 hours and 18 hours,
cooling to a temperature advantageously between 10° C. and 30° C., for example to 30° C., and
isolation of the diastereoisomerically enriched and purified hexaacid gadolinium complex of formula (I), for example by filtration and drying.

Step b4) is made possible by the fact that the isomers I-RRR and I-SSS are the most stable in basic medium. Such basic conditions promote the formation of gadolinium hydroxide, and consequently the decomplexation of the least stable isomers.

Thus, it should be noted that, surprisingly, the isomers I-RRR and I-SSS are more stable both in acidic medium, which allows the isomerization step b1), and in basic medium, which allows the selective decomplexation step b4).

In a preferred embodiment, the diastereoisomerically enriched complex obtained on conclusion of step b) according to any one of the variants described above has at least 85%, notably at least 90%, in particular at least 95%, preferably at least 97%, advantageously at least 98%, more advantageously at least 99% of the diastereoisomeric excess comprising the mixture of isomers I-RRR and I-SSS.

Preferably, said diastereoisomeric excess is constituted of at least 70%, notably of at least 80%, advantageously of at least 90%, preferably of at least 95% of the mixture of isomers I-RRR and I-SSS.

Advantageously, said diastereoisomeric excess consists of the mixture of isomers I-RRR and I-SSS.

The term "mixture of isomers I-RRR and I-SSS" also covers, by extension, the case where only one of the isomers, whether it be I-RRR or I-SSS, is present. However, the term "mixture of isomers I-RRR and I-SSS" preferentially denotes all the cases in which each of the isomers I-RRR and I-SSS is present in a variable but non-zero amount.

In a preferred embodiment, the isomers I-RRR and I-SSS are present in said mixture in a ratio of between 65/35 and 35/65, notably between 60/40 and 40/60, in particular between 55/45 and 45/55. Advantageously, the mixture of isomers I-RRR/I-SSS is a racemic (50/50) mixture.

Step c)

Step c) aims at forming the complex of formula (II) from its precursor, the diastereoisomerically enriched hexaacid gadolinium complex of formula (I) obtained in step b).

During this step, the three carboxylic acid functions of the hexaacid complex of formula (I) borne by the carbon atoms located in the y position on the side chains of the complex, relative to the nitrogen atoms of the macrocycle on which said side chains are grafted, are converted into amide functions, via an amidation reaction with 3-amino-1,2-propanediol, in racemic or enantiomerically pure form, preferably in racemic form.

This amidation reaction does not modify the absolute configuration of the three asymmetric carbon atoms located in the a position on the side chains, relative to the nitrogen atoms of the macrocycle onto which said side chains are grafted. Consequently, step c) makes it possible to obtain the complex of formula (II) with a diastereoisomeric excess comprising a mixture of the isomers II-RRR and II-SSS that is identical to the diastereoisomeric excess comprising a mixture of the isomers I-RRR and I-SSS with which is obtained the diastereoisomerically enriched hexaacid gadolinium complex of formula (I) obtained on conclusion of step b), which is at least 80%.

In a preferred embodiment, the complex of formula (II) obtained on conclusion of step c) has at least 85%, notably at least 90%, in particular at least 92%, preferably at least 94%, advantageously at least 97%, more advantageously at least 99% of the diastereoisomeric excess comprising the mixture of isomers II-RRR and II-SSS.

Preferably, said diastereoisomeric excess is constituted of at least 70%, notably of at least 80%, advantageously of at least 90%, preferably of at least 95% of the mixture of isomers II-RRR and II-SSS.

Advantageously, said diastereoisomeric excess consists of the mixture of isomers II-RRR and II-SSS.

The term "mixture of isomers II-RRR and II-SSS" also covers, by extension, the case where only one of the isomers, whether it be II-RRR or II-SSS, is present. However, the term "mixture of isomers I-RRR and I-SSS" preferentially denotes all the cases in which each of the isomers I-RRR and I-SSS is present in a variable but non-zero amount.

In a preferred embodiment, the isomers II-RRR and II-SSS are present in said mixture in a ratio of between 65/35 and 35/65, notably between 60/40 and 40/60, in particular between 55/45 and 45/55. Advantageously, the isomers II-RRR and II-SSS are present in the mixture in a 50/50 ratio.

The amidation reaction may be performed according to any method that is well known to those skilled in the art, notably in the presence of an agent for activating carboxylic acid functions and/or by acid catalysis.

It may notably be performed according to the methods described in EP 1 931 673, notably in paragraph [0027] of said patent.

In one particular embodiment, step c) comprises the activation of the carboxylic acid (—COOH) functions of the hexaacid complex of formula (I) borne by the carbon atoms located in the y position on the side chains of the complex, relative to the nitrogen atoms of the macrocycle on which said side chains are grafted, in the form of functional derivatives including a carbonyl (C=O) group, which are such that the carbon atom of the carbonyl group is more electrophilic than the carbon atom of the carbonyl group of the carboxylic acid functions. Thus, according to this particular embodiment, said carboxylic acid functions may notably be activated in the form of ester, acyl chloride or acid anhydride functions, or in any activated form that can lead to an amide bond. The activated forms that can lead to an amide bond are well known to those skilled in the art and may be obtained, for example, by the set of methods known in peptide chemistry for creating a peptide bond. Examples of such methods are given in the publication *Synthesis of peptides and peptidomimetics* volume E22a, pages 425-588, Houben-Weyl et al., Goodman Editor, Thieme-Stuttgart-New York (2004), and, among these examples, mention may be made notably of the methods of activation of carboxylic acids via an azide (acyl azide), for example via the action of a reagent such as diphenylphosphoryl azide (commonly referred to by the abbreviation DPPA), the use of carbodiimides alone or in the presence of catalysts (for example N-hydroxysuccinimide and derivatives thereof), the use of a carbonyldiimidazole (1,1'-carbonyldiimidazole, CDI), the use of phosphonium salts such as benzotriazol-1-yloxytris (dimethylamino)phosphonium hexafluorophosphate (commonly referred to by the abbreviation BOP), or else uroniums such as 2-(1H-benzotriazol-1-yl)-1,1,3,3-tetramethyluronium hexafluorophosphate (commonly referred to by the abbreviation HBTU).

Preferably, step c) comprises the activation of the above-mentioned carboxylic acid (—COOH) functions in the form of ester, acyl chloride or acid anhydride functions.

This embodiment is preferred to peptide coupling by activation of the carboxylic acid function using a coupling agent such as EDCl/HOBT as described in EP 1 931 673. Indeed, such coupling leads to the formation of one equivalent of 1-ethyl-3-[3-(dimethylamino)propyl]urea, which must be removed, notably by chromatography on silica or by liquid/liquid extraction by adding a solvent. Independently of the increased complexity of the process caused by such an additional step, the use of such purification methods is not desirable, as discussed previously. Furthermore, the use of HOBT is in itself problematic, since it is an explosive product.

For the purposes of the present invention, the term "ester function" is intended to denote a —C(O)O— group. It may in particular be a group —C(O)O—$R_1$, in which $R_1$ corresponds to a ($C_1$-$C_6$)alkyl group.

For the purposes of the present invention, the term "($C_1$-$C_6$)alkyl group" means a linear or branched, saturated hydrocarbon-based chain containing 1 to 6 and preferably 1 to 4 carbon atoms. Examples that may be mentioned include methyl, ethyl, propyl, isopropyl, butyl, isobutyl, sec-butyl, tert-butyl, pentyl and hexyl groups.

For the purposes of the present invention, the term "acyl chloride function", also known as "acid chloride function" is intended to denote a —CO—Cl group.

For the purposes of the present invention, the term "acid anhydride function" is intended to denote a —CO—O—CO— group. It may in particular be a group —CO—O—CO—$R_2$, in which $R_2$ corresponds to a ($C_1$-$C_6$)alkyl group.

The reactions for converting a carboxylic acid function into an ester, acyl chloride or acid anhydride function are well known to a person skilled in the art, who will be able to perform them according to any usual method with which he is familiar.

The complex of formula (II) is then obtained by aminolysis of the carboxylic acid functions activated in the form of ester, acyl chloride or acid anhydride functions, notably esters or acid anhydrides, preferably esters, by reaction with 3-amino-1,2-propanediol, in racemic or enantiomerically pure form, preferably in racemic form.

Preferentially, the steps of activating the carboxylic acid functions and of aminolysis are performed according to a one-pot embodiment, i.e. in the same reactor and without an intermediate step of isolation or purification of the intermediate including the carboxylic acid functions activated in the form of ester, acyl chloride or acid anhydride functions, notably esters or acid anhydrides, preferably esters.

According to a particular embodiment, step c) comprises the following successive steps:

c1) formation of an activated complex of formula (VII),

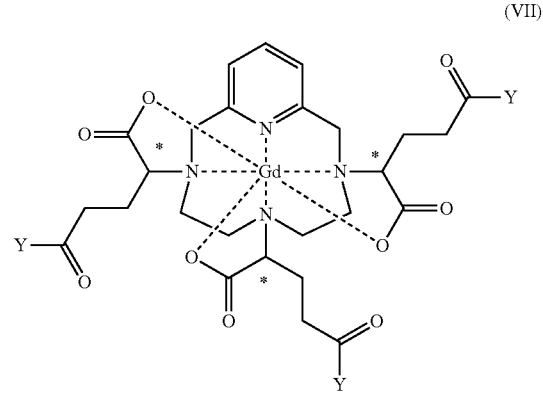

(VII)

in which Y represents a chlorine atom, a group —$OR_1$ or —O—C(O)—$R_2$; preferably, Y represents a group —$OR_1$ or —O—C(O)—$R_2$, with $R_1$ and $R_2$ corresponding, independently of each other, to a ($C_1$-$C_6$)alkyl group, and c2) aminolysis of the activated complex of formula (VII) with 3-amino-1,2-propanediol.

As will be clearly apparent to a person skilled in the art, the reaction for formation of the activated complex of formula (VII) does not modify the absolute configuration of the three asymmetric carbon atoms located in the a position on the side chains, relative to the nitrogen atoms of the macrocycle onto which said side chains are grafted. Consequently, step c1) makes it possible to obtain the activated complex of formula (VII) with a diastereoisomeric excess comprising a mixture of the isomers VII-RRR and VII-SSS, of formulae (VII-RRR) and (VII-SSS) represented below, that is identical to the diastereoisomeric excess comprising a mixture of the isomers I-RRR and I-SSS with which is obtained the diastereoisomerically enriched hexaacid gadolinium complex of formula (I) obtained on conclusion of step b), which is at least 80%.

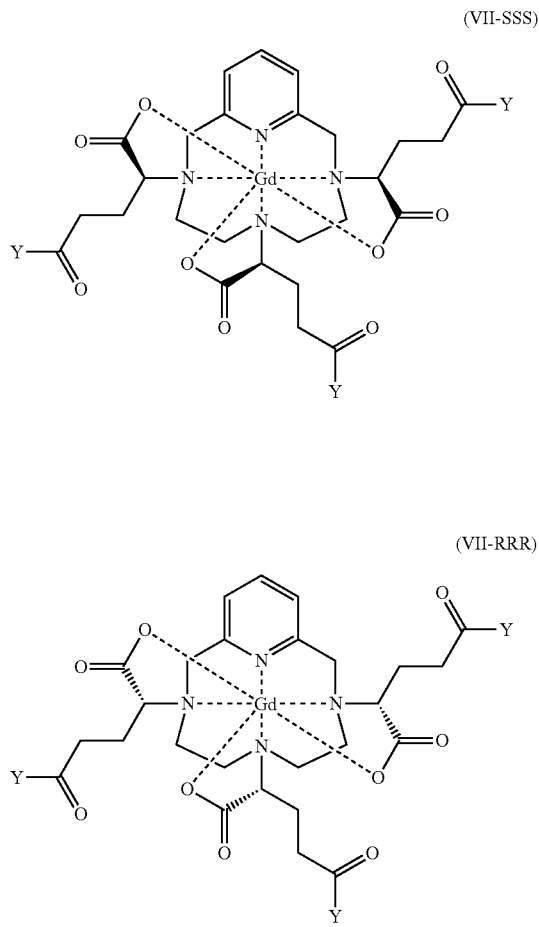

In the case where Y represents a chlorine atom, step c1) is typically performed by reaction between the diastereoisomerically enriched hexaacid gadolinium complex of formula (I) obtained in step b) and thionyl chloride (SOCl$_2$).

In the case where Y represents an —O—C(O)—CH$_3$ group, step c1) is typically performed by reaction between the diastereoisomerically enriched hexaacid gadolinium complex of formula (I) obtained in step b) and acetyl chloride.

In an advantageous embodiment, step c) comprises the activation of the abovementioned carboxylic acid (—COOH) functions in the form of ester functions.

According to this embodiment, step c) may more particularly comprise the following successive steps:
c1) formation of a triester of formula (VIII),

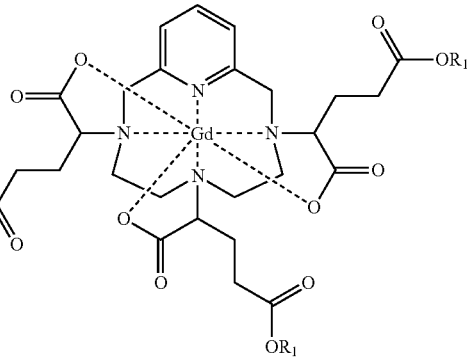

in which R$_1$ represents a (C1-C$_6$)alkyl group, and
c2) aminolysis of the triester of formula (VIII) with 3-amino-1,2-propanediol.

Step c1) is typically performed in the alcohol of formula R$_1$OH, which acts both as solvent and as reagent, in the presence of an acid such as hydrochloric acid.

In a first stage, the hexaacid gadolinium complex of formula (I) and the alcohol R$_1$OH are placed in the reactor. The reaction medium is then cooled to a temperature below 10° C., notably below 5° C., typically to 0° C., and an acidic solution of the alcohol R$_1$OH, typically of hydrochloric acid in R$_1$OH, is then gradually added. The reaction medium is kept stirring at room temperature (i.e. at a temperature between 20 and 25° C.) for a time typically greater than 5 hours, preferably between 10 hours and 20 hours. The reaction medium is cooled to a temperature below 10° C., notably between 0° C. and 5° C., prior to step c2).

Step c2) is also typically performed in the alcohol of formula R$_1$OH, in the presence of an acid such as hydrochloric acid.

Thus, steps c1) and c2) may be readily performed according to a one-pot embodiment. Advantageously, the triester of formula (VII) is not isolated between steps c1) and c2).

However, in order to promote the aminolysis reaction, in step c2), the alcohol of formula R$_1$OH is preferably removed by vacuum distillation.

For the purposes of the present invention, the term "vacuum distillation" means the distillation of a mixture performed at a pressure of between 10 and 500 mbar, notably between 10 and 350 mbar, preferably between 10 and 150 mbar, in particular between 50 and 100 mbar.

Similarly, in order to promote the aminolysis reaction, in step c2), 3-amino-1,2-propanediol is introduced in large excess. Typically, the material amount of 3-amino-1,2-propanediol introduced is greater than 4 eq., notably greater than 7 eq., advantageously greater than 10 eq., relative to the material amount of diastereoisomerically enriched hexaacid gadolinium complex of formula (I) initially introduced in step c), which itself corresponds to 1 equivalent.

Surprisingly, despite the acidic conditions typically employed in steps c1) and c2), which should increase the kinetic instability of the gadolinium complexes, no decomplexation or isomerization of the triester of formula (VIII) is observed. The desired triamide is obtained with a very good degree of conversion and the absolute configuration of the three asymmetric carbon atoms located in the a position on the side chains, relative to the nitrogen atoms of the macrocycle, is conserved.

Moreover, it should be noted that, in general, amidation reactions by direct reaction between an ester and an amine are very sparingly described in the literature (see on this subject K. C. Nadimpally et al., *Tetrahedron Letters*, 2011, 52, 2579-2582).

In a preferred embodiment, step c) comprises the following successive steps:

c1) formation of a methyl triester of formula (IV),

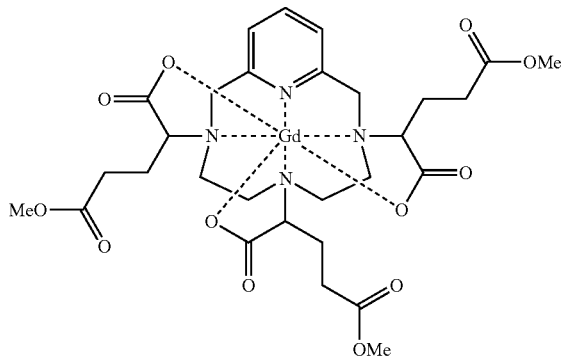

(IV)

notably by reaction in methanol in the presence of an acid such as hydrochloric acid, and c2) aminolysis of the methyl triester of formula (IV) with 3-amino-1,2-propanediol, notably in methanol in the presence of an acid such as hydrochloric acid.

Advantageously, the methyl triester of formula (IV) is not isolated between steps c1) and c2).

In a preferred embodiment, in step c2), the methanol is removed by vacuum distillation, until a temperature typically greater than 55° C., notably between 60° C. and 65° C. is reached, and the reaction medium is maintained at this temperature under vacuum for a time typically greater than 5 hours, notably between 10 hours and 20 hours, before being cooled to room temperature and diluted with water.

The present invention encompasses all the combinations of the particular, advantageous or preferred embodiments described above in connection with each step of the process.

The present invention also relates to a triester gadolinium complex of formula (VIII):

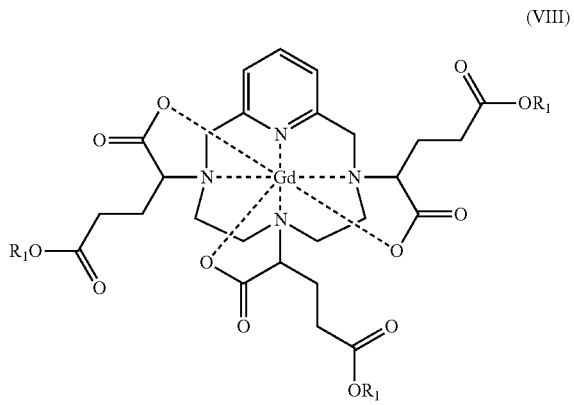

(VIII)

constituted of at least 80% of a diastereoisomeric excess comprising a mixture of isomers VIII-RRR and VIII-SSS of formulae:

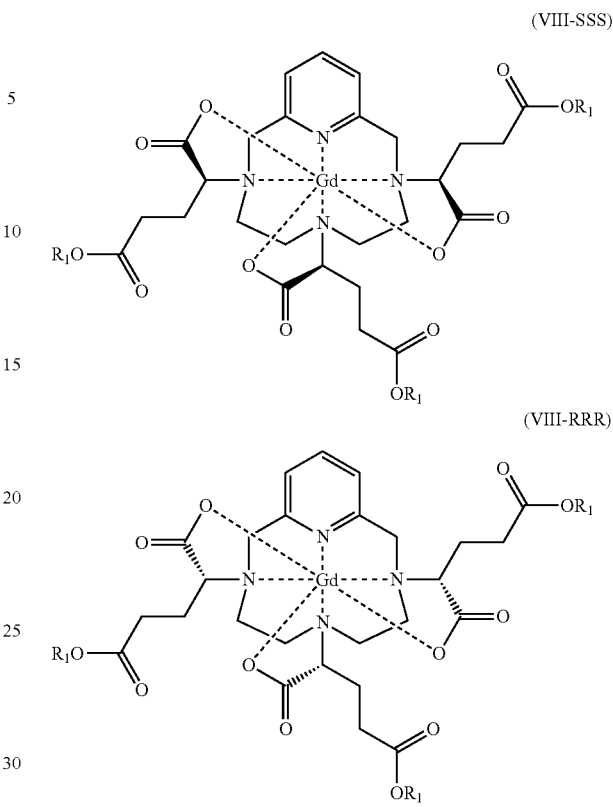

(VIII-SSS)

(VIII-RRR)

In the context of the present invention, the term "diastereoisomeric excess" is intended to denote, as regards the triester gadolinium complex of formula (VIII), the fact that said complex is predominantly present in the form of an isomer or group of isomers chosen from the diastereoisomers VIII-RRR, VIII-SSS, VIII-RRS, VIII-SSR, VIII-RSS, VIII-SRR, VIII-RSR and VIII-SRS. Said diastereoisomeric excess is expressed as a percentage and corresponds to the amount represented by the predominant isomer or group of isomers relative to the total amount of the triester complex of formula (VIII). It is understood that this percentage may be on either a molar or mass basis, since isomers have, by definition, the same molar mass.

In one particular embodiment, the triester gadolinium complex of formula (VIII) according to the invention has at least 85%, notably at least 90%, in particular at least 95%, preferably at least 97%, advantageously at least 98%, more advantageously at least 99% of the diastereoisomeric excess comprising the mixture of isomers VIII-RRR and VIII-SSS.

Preferably, said diastereoisomeric excess is constituted of at least 70%, notably of at least 80%, advantageously of at least 90%, preferably of at least 95% of the mixture of isomers VIII-RRR and VIII-SSS.

Advantageously, said diastereoisomeric excess consists of the mixture of isomers VIII-RRR and VIII-SSS.

The term "mixture of isomers VIII-RRR and VIII-SSS" also covers the case where only one of the isomers, whether it be VIII-RRR or VIII-SSS, is present. However, the term "mixture of isomers VIII-RRR and VIII-SSS" preferentially denotes all the cases in which each of the isomers VIII-RRR and VIII-SSS is present in a variable but non-zero amount.

In a preferred embodiment, the isomers VIII-RRR and VIII-SSS are present in said mixture in a ratio of between 65/35 and 35/65, notably between 60/40 and 40/60, in particular between 55/45 and 45/55. Advantageously, the mixture of isomers VIII-RRR/VIII-SSS is a racemic (50/50) mixture.

In a preferred embodiment, the triester gadolinium complex of formula (VIII) according to the invention is a trimethyl gadolinium complex, i.e. a triester gadolinium complex of formula (VIII) in which $R_1$ is a methyl group ($CH_3$).

Preparation of the Hexaacid of Formula (III)

The hexaacid of formula (III), which participates in step a) of the process for preparing the complex of formula (II) according to the invention, may be prepared according to any method already known and notably according to the methods described in EP 1 931 673.

However, according to a preferred embodiment, the hexaacid of formula (III) is obtained by alkylation of the pyclene of formula (V):

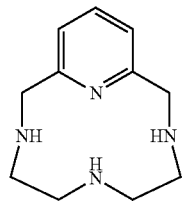

(V)

with a compound of formula $R_3OOC\text{—}CHG_p\text{-}(CH_2)_2\text{—}COOR_4$ (IX), in which:
- $R_3$ and $R_4$ represent, independently of each other, a ($C_3$-$C_6$)alkyl group, notably a ($C_4$-$C_6$)alkyl group such as a butyl, isobutyl, sec-butyl, tert-butyl, pentyl or hexyl group, and
- $G_p$ represents a leaving group such as a tosylate or triflate group, or a halogen atom, preferably a bromine atom, to obtain the hexaester of formula (X)

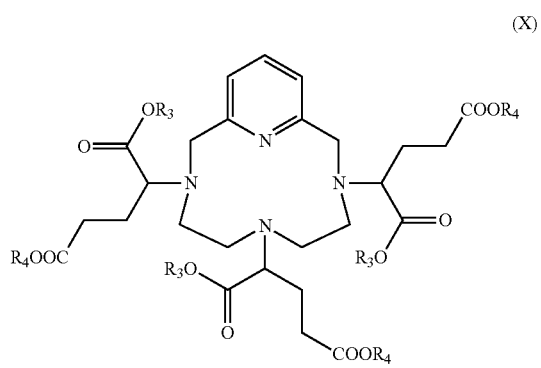

(X)

followed by a hydrolysis step, leading to said hexaacid of formula (III).

In a preferred embodiment, $R_3$ and $R_4$ are identical.

According to an advantageous embodiment, the hexaacid of formula (III) is obtained by alkylation of the pyclene of formula (V):

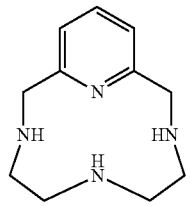

(V)

with dibutyl 2-bromoglutarate, to obtain the butyl hexaester of formula (VI):

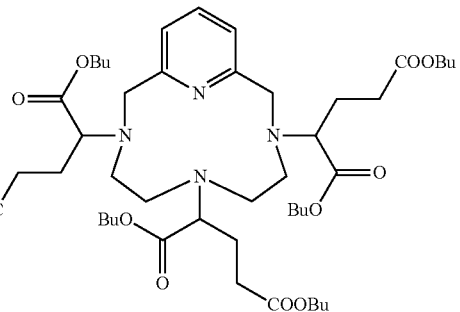

(VI)

followed by a hydrolysis step, leading to said hexaacid of formula (III).

The dibutyl 2-bromoglutarate used is in racemic or enantiomerically pure form, preferably in racemic form.

The use of dibutyl 2-bromoglutarate is particularly advantageous, in comparison with the use of ethyl 2-bromoglutarate described in EP 1 931 673. Indeed, commercial diethyl 2-bromoglutarate is a relatively unstable compound, which degrades over time and under the effect of the temperature. More precisely, this ester has a tendency to become hydrolysed or to cyclize and thus to lose its bromine atom. Attempts to purify commercial diethyl 2-bromoglutarate, or to develop new synthetic routes for obtaining it with improved purity, and thus to prevent its degradation, were unsuccessful.

The alkylation reaction is typically performed in a polar solvent, preferably in water, in particular in deionized water, advantageously in the presence of a base such as potassium or sodium carbonate.

The use of water is preferred notably to that of acetonitrile, described in EP 1 931 673, for obvious reasons.

The reaction is advantageously performed at a temperature of between 40° C. and 80° C., typically between 50° C. and 70° C. and notably between 55° C. and 60° C., for a time of between 5 hours and 20 hours, in particular between 8 hours and 15 hours.

The hydrolysis step is advantageously performed in the presence of an acid or a base, advantageously a base such as sodium hydroxide. The hydrolysis solvent may be water, an alcohol such as ethanol, or a water/alcohol mixture. This step is advantageously performed at a temperature of between 40° C. and 80° C., typically between 40° C. and 70° C. and notably between 50° C. and 60° C., typically for a time of between 10 hours and 30 hours, in particular between 15 hours and 25 hours.

The present invention furthermore relates to the butyl hexaester of formula (VI):

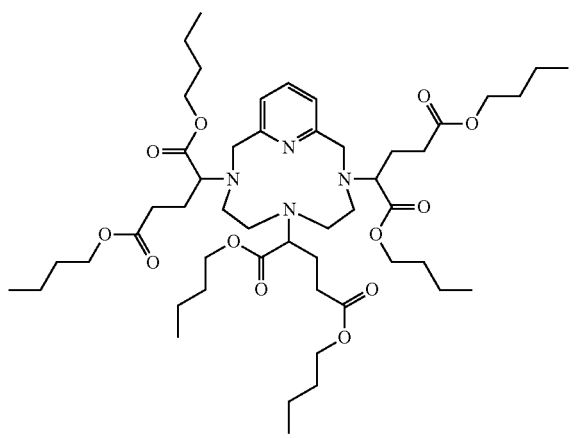

(VI)

Specifically, this hexaester is distinguished by stability that is markedly improved relative to esters having a shorter alkyl chain, notably relative to the ethyl hexaester described in EP 1 931 673.

FIGURES

FIG. 1: degradation under basic conditions of the groups of isomers iso1 to iso4 of the complex of formula (II), expressed as an area percentage of a given group of isomers over time.

EXAMPLES

The examples given below are presented as non-limiting illustrations of the invention.

Separation of the Groups of Isomers isoA, isoB, isoC and isoD of the Hexaacid Gadolinium Complex of Formula (I) by HPLC An HPLC machine constituted of a pumping system, an injector, a chromatography column, a UV spectrophotometric detector and a data processing and control station is used. The chromatography column used is a C18-250×4.6 mm-5 μm column (Symmetry® range from Waters).

Mobile Phase:
Route A: 100% acetonitrile and Route B: aqueous solution of $H_2SO_4$ (96%) at 0.1% v/v Preparation of the Test Solutions:
Solution of the hexaacid gadolinium complex of formula (I) at 10 mg/mL in purified water Analytical Conditions:

| Column temperature | 25° C. |
|---|---|
| Sample temperature | Room temperature (20-25° C.) |
| Flow rate | 1.0 ml/min |
| Injection volume | 20 μl |
| UV detection | 200 nm |
| Analysis time | 60 min |

Gradient:

| Time | % Acn | % $H_2SO_4$ 0.1% |
|---|---|---|
| 0 | 1 | 99 |
| 10 | 5 | 95 |
| 40 | 10 | 90 |
| 50 | 25 | 75 |
| 55 | 1 | 99 |
| 60 | 1 | 99 |

% Acn: % v/v of acetonitrile in the mobile phase
% $H_2SO_4$ 0.1%: % v/v of the solution of $H_2SO_4$ at 0.1% v/v in the mobile phase Four main peaks are obtained. Peak 4 of the HPLC plot, namely isoD, corresponds to a retention time of 35.7 minutes.

Separation of the Groups of Isomers isoA, isoB, isoC and isoD of the Hexaacid Gadolinium Complex of Formula (I) by UHPLC A UHPLC machine constituted of a pumping system, an injector, a chromatography column, a UV detector and a data station is used. The chromatography column used is a UHPLC 150×2.1 mm-1.8 μm column (Waters Acquity UPLC HSS T3 column). It is a reverse-phase UPLC column containing spherical particles constituted of silica with tri-functional C18 (octadecyl) grafting, and the silanols of which have been treated with capping agents (end-capped). It is also characterized by a length of 150 mm, an inside diameter of 2.1 mm, a particle size of 1.8 μm, a porosity of 100 Å and a carbon content of 11%.

Preferentially, the stationary phase used should be compatible with the aqueous mobile phases.

Mobile Phase:
Route A: 100% acetonitrile and Route B: aqueous solution of $H_2SO_4$ (96%) at 0.1% v/v Preparation of the Test Solutions:
Solution of the hexaacid gadolinium complex of formula (I) at 0.8 mg/mL in purified water Analytical Conditions:

| Column temperature | 35° C. |
|---|---|
| Sample temperature | Room temperature (20-25° C.) |
| Flow rate | 0.4 mL/min |
| Injection volume | 10 μl |
| UV detection | 200 nm |
| Analysis time | 32 min |

Gradient:

| Time | % Acn | % $H_2SO_4$ 0.1% |
|---|---|---|
| 0 | 1 | 99 |
| 14 | 8 | 92 |
| 20 | 11 | 89 |
| 25 | 25 | 75 |
| 27 | 1 | 99 |
| 32 | 1 | 99 |

Four main peaks are obtained. Peak 4 of the UHPLC plot, namely isoD, corresponds to a retention time of 17.4 minutes.

Separation of the Groups of Isomers Iso1, Iso2, Iso3 and Iso4 of the Complex of Formula (II) by UHPLC A UHPLC machine constituted of a pumping system, an injector, a chromatography column, a UV detector and a data station is used. The chromatography column used is a UHPLC 150×2.1 mm-1.6 μm column (Waters Cortecs® UPLC T3 column).

Mobile Phase:
Route A: 100% acetonitrile and Route B: aqueous solution of $H_2SO_4$ (96%) at 0.0005% v/v
Preparation of the Test Solutions:
Solution of the complex of formula (II) at 2 mg/mL in purified water
Analytical Conditions:

| Column temperature | 40° C. |
|---|---|
| Sample temperature | Room temperature (20-25° C.) |
| Flow rate | 0.3 mL/min |
| Injection volume | 1 µl |
| UV detection | 200 nm |
| Analysis time | 20 min |

Gradient:

| Time | % Acn | % $H_2SO_4$ 0.0005% |
|---|---|---|
| 0 | 1 | 99 |
| 3 | 5 | 95 |
| 12 | 10 | 90 |
| 15 | 25 | 75 |
| 16 | 1 | 99 |
| 20 | 1 | 99 |

Four main peaks are obtained. Peak 4 of the UHPLC plot, namely iso4, corresponds to a retention time of 6.3 minutes.
Relaxivity Measurements The relaxation times $T_1$ and $T_2$ were determined via standard procedures on a Minispec® mq20 machine (Bruker) at 20 MHz (0.47 T), at 60 MHz (1.41 T) and 37° C. The longitudinal relaxation time $T_1$ is measured using an inversion recovery sequence and the transverse relaxation time $T_2$ is measured via the CPMG (Carr-Purcell-Meiboom-Gill) technique.

The relaxation rates $R_1$ ($=1/T_1$) and $R_2$ ($=1/T_2$) were calculated for different concentrations of total metal (ranging from $0.5 \times 10^{-3}$ to $5 \times 10^{-3}$ mol/L) in aqueous solution at 37° C. The correlation between $R_1$ or $R_2$ as a function of the concentration is linear, and the slope represents the relaxivity $r_1$ ($R_1/C$) or $r_2$ ($R_2/C$) expressed in (1/second)×(1/mMol/L), i.e. ($mM^{-1} \cdot s^{-1}$).
Measurement of the Kinetic Inertia of the Groups of Isomers of the Complex of Formula (II) in Acidic Medium The dissociation of the gadolinium complexes present in the four unresolved peaks of isomers iso1 to iso4 ($C=8 \times 10^{-6}$ M) is studied at 37° C., pH 1.2 in a hydrochloric acid solution under pseudo-first order kinetic conditions without control of the ionic strength by monitoring the release of gadolinium into the solution. The amount of free gadolinium was determined by spectrometry at 654 nm after adding a solution of Arsenazo III ($C=5.3 \times 10^{-4}$ M).

The half-life times ($T_{1/2}$) that were determined for each of the groups of isomers are collated in the table below:

| Groups of isomers | $T_{1/2}$ (pH 1.2-37° C.) |
|---|---|
| Iso1 | 18 hours |
| Iso2 | 6 hours |
| Iso3 | 8 days |
| Iso4 | 27 days |

Study of Depredation Under Basic Conditions of the Groups of Isomers of the Complex of Formula (II)

The complex of formula (II) will be referred to as AP in the rest of this example.

The kinetics of degradation of the unresolved peaks of isomers iso1 to iso4, referred to by the generic term isoX, are evaluated by measuring the HPLC purity and by monitoring the area of each unresolved peak of isomers over time. The magnitudes measured are thus:
$P_{HPLC}$ (time), and $$\frac{Area_{IsoX}(t)}{Area_{IsoX}(t_0)} \qquad \text{[Math 1]}$$

The degradation conditions chosen are the following: [AP]=1 mM in 0.1 N sodium hydroxide. Under these dilution conditions, the impact of the degradation of AP on the experimental medium is low. The degradation products do not modify the pH of the medium, this parameter being critical in the study of the degradation kinetics. This is confirmed experimentally by measuring the initial pH and the pH at the end of degradation (72 hours, 37° C.):

|  | Solution of AP |
|---|---|
| pH of 0.1N NaOH ($T_0$) | 12.9 |
| pH (after 72 hours at 37° C.) | 12.8 |

The method for preparing the solutions is described below:
weigh out about 0.05 g of each product qs 10 mL of mQ water, to obtain a solution A such that $[AP]_A$=5 mM,
dilution: 2 mL of solution A qs 10 mL NaOH (0.1 N), to obtain a solution B such that $[AP]_B$=1 mM and [NaOH]=0.08 M,
aliquot of the solutions in HPLC flasks, and
incubation of the HPLC flasks containing the solutions of AP in NaOH at the study temperature (37° C.).

For each point, an aliquot is taken and analysed by HPLC without dilution of the sample (ammonium acetate method).
The results obtained are given in FIG. 1.
Preparation of the Butyl Hexaester of Formula (VI)

184 kg (570 mol) of dibutyl 2-bromoglutarate and 89 kg (644 mol) of potassium carbonate are mixed in a reactor and heated to 55-60° C. An aqueous solution of 29.4 kg (143 mol) of pyclene in 24 kg of water is added to the preceding preparation. The reaction mixture is maintained at 55-60° C. and then refluxed for about 10 hours. After reaction, the medium is cooled, diluted with 155 kg of toluene and then washed with 300 litres of water. The butyl hexaester is extracted into the aqueous phase with 175 kg (1340 mol) of phosphoric acid (75%). It is then washed three times with 150 kg of toluene. The butyl hexaester is re-extracted into a toluene phase by dilution with 145 kg of toluene and 165 kg of water, followed by basification with 30% sodium hydroxide (m/m) to reach a pH of 5-5.5. The lower aqueous phase is removed. The butyl hexaester is obtained by concentrating to dryness under vacuum at 60° C., in a yield of about 85%.
Preparation of the Hexaacid of Formula (III)

113 kg (121 mol) of butyl hexaester are placed in a reactor along with 8 kg of ethanol. The medium is brought to 55±5° C. and 161 kg (1207.5 mol) of 30% sodium hydroxide (m/m) are then added over 3 hours. The reaction mixture is maintained at this temperature for about 20 hours. The butanol is then removed by decantation of the reaction medium. The hexaacid of formula (III) obtained in sodium salt form is diluted with water to obtain an aqueous solution of about 10% (m/m). This solution is treated on an acidic cationic resin. The hexaacid of formula (III) in aqueous solution is obtained in a yield of about 90% and a purity of 95%.

Preparation of the Hexaacid Gadolinium Complex of Formula (I)

Experimental Protocol

Complexation and Isomerization

Without Acetic Acid 418 kg (117 kg of pure hexaacid of formula (III)/196 mol) of an aqueous solution of hexaacid of formula (III) at 28% by weight are placed in a reactor. The pH of the solution is adjusted to 2.7 by adding hydrochloric acid, and 37 kg (103.2 mol) of gadolinium oxide are then added. The reaction medium is heated at 100-102° C. for 48 hours to achieve the expected isomeric distribution of the hexaacid of formula (III).

With Acetic Acid

Gadolinium oxide (0.525 molar eq.) is suspended in a solution of hexaacid of formula (III) at 28.1% by mass.

99-100% acetic acid (50% by mass/pure hexaacid of formula (III)) is poured into the medium at room temperature.

The medium is heated to reflux followed by distillation up to 113° C. by mass by refilling the medium with acetic acid gradually as the water is removed. Once the temperature of 113° C. is reached, a sufficient amount of acetic acid to arrive at the starting volume is added.

The medium is maintained at 113° C. overnight.

Crystallization, Recrystallization

Crystallization

The hexaacid gadolinium complex of formula (I) in solution is cooled to 40° C., the primer is added and the agents are left in contact for at least 2 hours. The product is then isolated by filtration at 40° C. and washed with osmosed water.

Recrystallization 180 kg of the hexaacid gadolinium complex of formula (I) obtained previously (solids content of about 72%) are suspended in 390 kg of water. The medium is heated to 100° C. to dissolve the product, and then cooled to 80° C. to be primed by adding a small amount of primer. After cooling to room temperature, the hexaacid gadolinium complex of formula (I) is isolated by filtration and drying.

Selective Decomplexation

The dry product is placed in the reactor with osmosed water at 20° C. The mass of water added is equal to twice the theoretical mass of hexaacid gadolinium complex of formula (I). 30.5% sodium hydroxide (m/m) (6.5 eq.) is poured into the medium at 20° C. At the end of the addition of NaOH, the medium is left in contact at 50° C. for 16 hours. The medium is cooled to 25° C. and the product is filtered off on a bed of Clarcel.

Content of Diastereoisomeric Excess Comprising a Mixture of Diastereoisomers I-RRR and I-SSS The ratio in which the various isomers of the complex of formula (I) are present in the mixture of diastereoisomers depends on the conditions under which the complexation and isomerization steps are performed, as is seen in Table 3 below.

TABLE 3 content of the mixture I-RRR and I-SSS as a function of the complexation/isomerization conditions

| pH | Temperature | Content of hexaacid of formula (III) | Time | Diastereoisomeric excess comprising a mixture I-RRR and I-SSS |
|---|---|---|---|---|
| 5.7 | 80° C. | 40% | 3 hours | 19% |
| 3.5 | 90° C. | 50% | 10 hours | 49% |
| 3.0 | 101° C. | 40% | 10 hours | 68% |
| 2.7 | 101° C. | 28% | 48 hours | 98.04% |

The additional steps of recrystallization and selective decomplexation make it possible to increase the diastereoisomeric excess of the mixture I-RRR and I-SSS (see Table 4).

TABLE 4 content of diastereoisomeric excess comprising a mixture I-RRR and I-SSS after crystallization/recrystallization/selective decomplexation

| | After the first crystallization | After recrystallization | After selective decomplexation |
|---|---|---|---|
| Diastereoisomeric excess comprising a mixture I-RRR and I-SSS | 98.04% | 99.12% | 99.75% |

Preparation of the Complex of Formula (II)

90 kg (119 mol) of the hexaacid complex of formula (I) and 650 kg of methanol are placed in a reactor. The mixture is cooled to about 0° C. and 111 kg (252 mol) of a methanolic solution of hydrochloric acid (8.25% of HCl in methanol) are then poured in while maintaining the temperature at 0° C. The reaction medium is brought to room temperature and stirring is then continued for 16 hours. After cooling to 0-5° C., 120 kg (1319 mol) of 3-amino-1,2-propanediol are added. The reaction medium is then heated while distilling off the methanol under vacuum until a temperature of 60-65° C. is reached. The concentrate is maintained for 16 hours at this temperature under vacuum. At the end of contact, the medium is diluted with 607 kg of water while cooling to room temperature. The solution of the crude complex of formula (II) is neutralized with 20% hydrochloric acid (m/m). 978.6 kg of solution are thus obtained, with a concentration of 10.3%, representing 101 kg of material. The yield obtained is 86.5%.

Tests of Conversion of Isomers Starting with the Complexes of Formula (II)

The isomers of the complex of formula (II) were synthesized from the groups of isomers isoA, isoB, isoC and isoD of the hexaacid complex of formula (I) isolated by preparative HPLC. The four groups of isomers were isolated and then amidated with R and S 3-amino-1,2-propanediol (APD). Eight isomers were thus obtained:
isoA+APD(R) and isoA+APD(S),
isoB+APD(R) and isoB+APD(S),
isoC+APD(R) and isoC+APD(S), and
isoD+APD(R) and isoD+APD(S).

Each of these isomers was placed under conditions allowing isomerization of the hexaacid gadolinium complex of formula (I).

Thus, an HCl solution at pH 3 is prepared by diluting 1 mL of 1N HCl in 1 litre of water. The isomers are added at a concentration of 1 mM to the HCl solution at pH 3. 10 mg of powder are dissolved in 10 mL of this solution. The eight solutions obtained are heated to 100° C. and then analysed at $T_0$ and at $T_0+23$ hours by HPLC.

The purity percentages measured by HPLC are given in the table below.

| | isoA + APD(S) | isoB + APD(S) | isoC + APD(S) | isoD + APD(S) |
|---|---|---|---|---|
| $T_0$ | 95.4% | 92.3% | 91% | 98.6% |
| $T_0 + 23$ h | 86% | 83% | 84% | 92% |

The loss of purity is due to the chemical degradation (hydrolysis of the amide functions) of the product due to the conditions imposed by the isomerization reaction.

Since the conditions allowing the isomerization of the various compounds lead to substantial chemical degradation of the products via hydrolysis of the amide functions, the isomerization cannot be performed in a clean and selective manner directly on the complex of formula (II) obtained according to the process described in EP 1 931 673.

The invention claimed is:

1. A process for preparing the complex of formula (II) below:

(II)

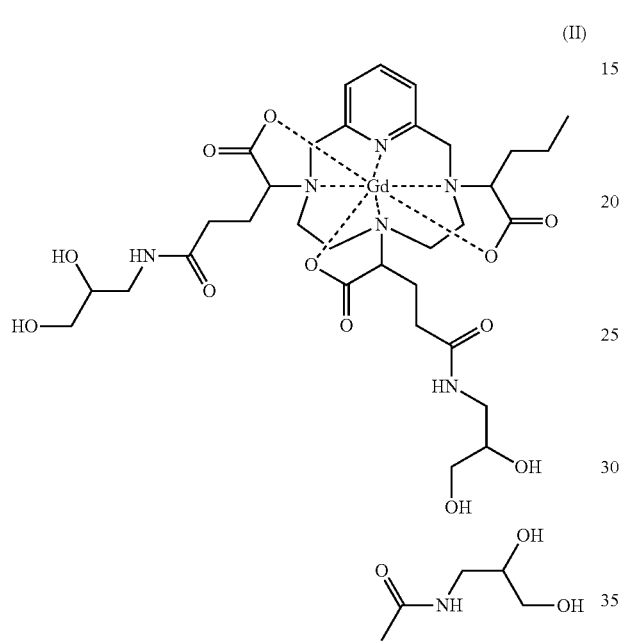

having a diastereoisomeric excess of at least 80% of a mixture of isomers II-RRR and II-SSS of formulae:

(II-SSS)

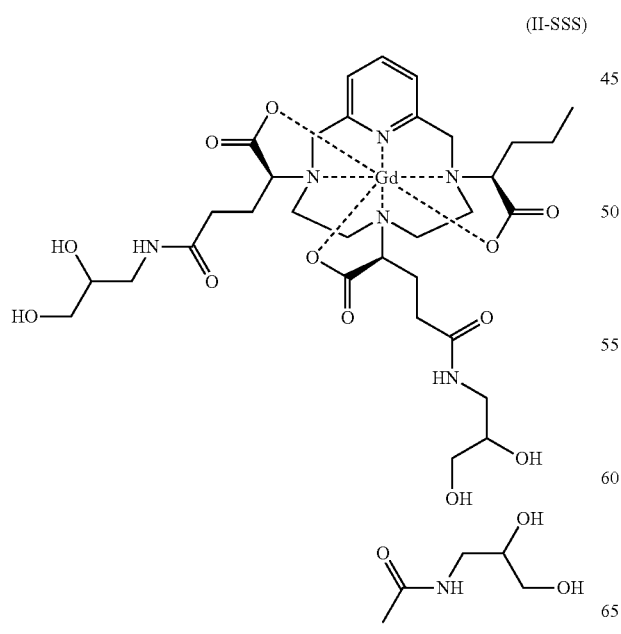

and (II-RRR)

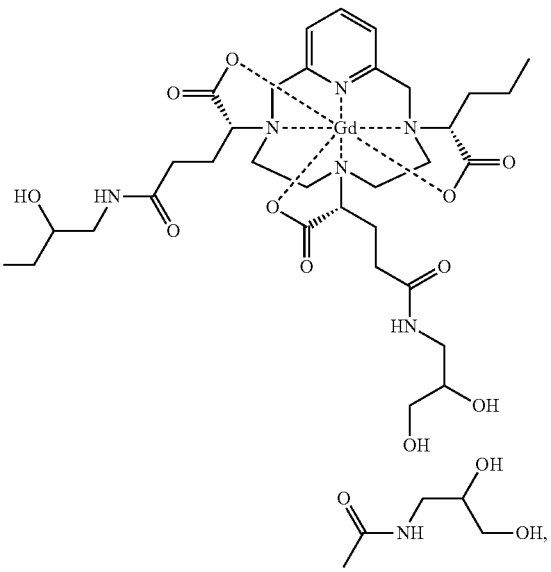

comprising:
a) complexing a hexaacid of formula (III) below:

(III)

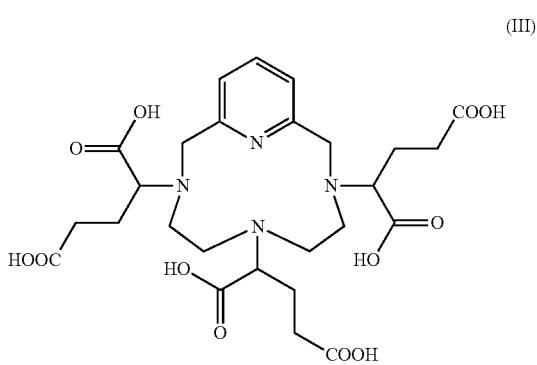 [SMILES: O=C(O)CCC(C(=O)O)N1CCN(C(CCC(=O)O)C(=O)O)Cc2cccc(n2)CN(C(CCC(=O)O)C(=O)O)CC1]

with gadolinium to obtain the hexaacid gadolinium complex of formula (I) below:

(I)

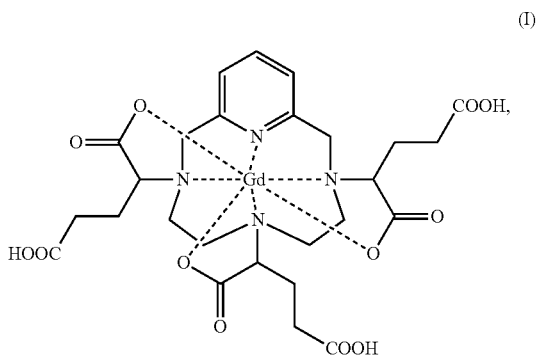

b) isomerizing by heating the hexaacid gadolinium complex of formula (I) in an aqueous solution at a pH from 2 to 4 to obtain a diastereoisomerically enriched complex having a diastereoisomeric excess of at least 80% of a mixture of isomers I-RRR and I-SSS of the hexaacid gadolinium complex of formula (I), of formulae:

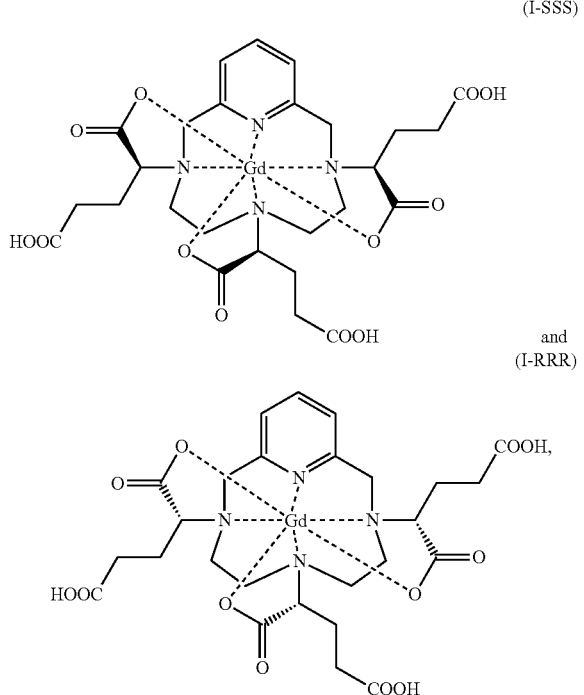

(I-SSS)

and (I-RRR)

and c) reacting the diastereoisomerically enriched complex with 3-amino-1,2-propanediol to form the complex of formula (II).

2. The process of claim 1, wherein the hexaacid gadolinium complex of formula (I) is isomerized without being isolated or purified.

3. The process of claim 1, wherein the aqueous solution of step b) contains acetic acid.

4. The process of claim 3, wherein step b) is performed at a temperature of from 100° C. to 120° C. and from 12 hours to 48 hours.

5. The process of claim 1, wherein step b) comprises:
b1) isomerizing by heating the hexaacid gadolinium complex of formula (I) in an aqueous solution at a pH of from 2 to 4 to obtain the diastereoisomerically enriched complex, and
b2) isolating the diastereoisomerically enriched complex by crystallization.

6. The process of claim 5, wherein the crystallization is performed by seeding.

7. The process of claim 5, further comprising selectively decomplexing diastereoisomers of the complex of formula (I) other than the diastereoisomers I-RRR and I-SSS.

8. The process of claim 5, wherein step b) further comprises:
b3) purifying by crystallization the isolated diastereoisomerically enriched complex obtained in step b2).

9. The process of claim 1, wherein the diastereoisomerically enriched complex obtained in step b) has a diastereoisomeric excess of at least 85%.

10. The process of claim 1, wherein the diastereoisomerically enriched complex obtained in step b) has a diastereoisomeric excess of at least 90%.

11. The process of claim 5, wherein the diastereoisomerically enriched complex obtained in step b) has a diastereoisomeric excess of at least 95%.

12. The process of claim 1, wherein step c) comprises:
c1) reacting the diastereoisomerically enriched complex obtained in step b) with an alcohol of formula $R_1OH$ in the presence of an acid to form a triester of formula (VIII) below,

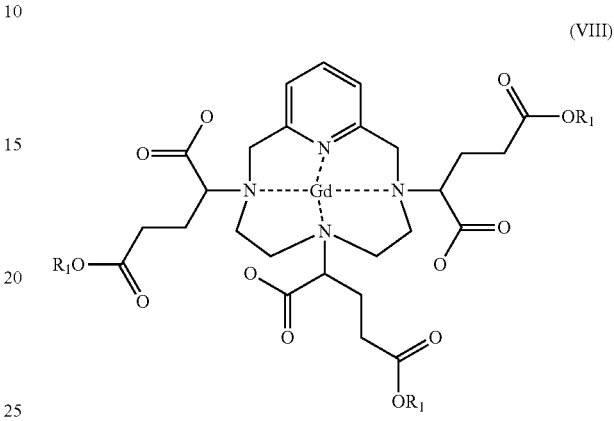

(VIII)

in which $R_1$ represents a $(C_1$-$C_6)$ alkyl group, and
c2) aminolysing the triester of formula (VIII) with 3-amino-1,2-propanediol in the presence of an acid.

13. The process of claim 12, wherein the triester of formula (VIII) is not isolated between step c1) and step c2).

14. The process of claim 12, wherein $R_1$ represents a methyl group.

15. The process of claim 12, wherein step c) comprises:
c1) reacting the diastereoisomerically enriched complex obtained in step b) with methanol in the presence of an acid to form the methyl triester of formula (IV) below, and

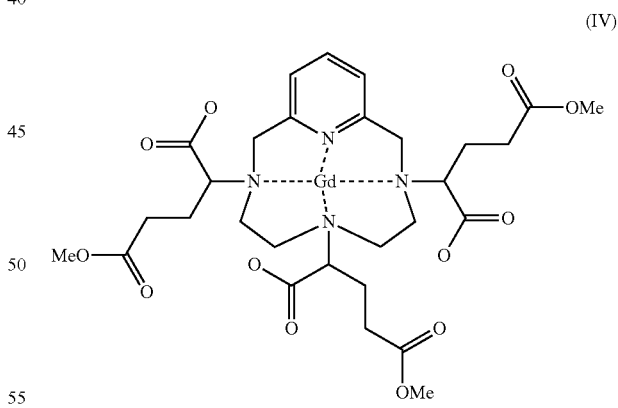

(IV)

c2) aminolysing the methyl triester of formula (IV) with 3-amino-1,2-propanediol in methanol in the presence of an acid, wherein the methanol is removed by vacuum distillation, until a temperature of greater than 55° C. is reached, the reaction medium being maintained at this temperature under vacuum for a time greater than 5 hours, before being cooled to room temperature and diluted with water.

16. The process of claim 15, wherein the hexaacid of formula (III) is obtained by alkylating the pyclene of formula (V):

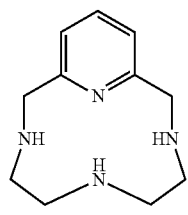
with dibutyl 2-bromoglutarate, to obtain the butyl hexaester of formula (VI):
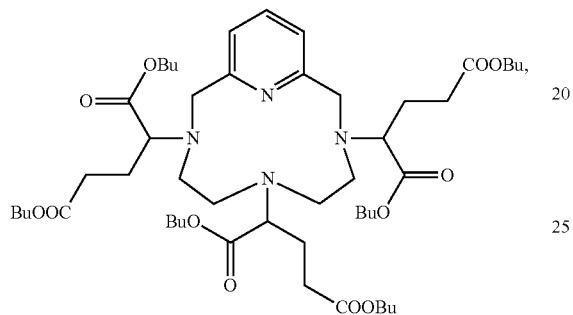
and
hydrolyzing the butyl hexaester of formula (VI) to obtain the hexaacid of formula (III).

UNITED STATES PATENT AND TRADEMARK OFFICE
CERTIFICATE OF CORRECTION

PATENT NO. : 11,426,470 B2  
APPLICATION NO. : 17/397022  
DATED : August 30, 2022  
INVENTOR(S) : Soizic Le Greneur et al.

Page 1 of 2

It is certified that error appears in the above-identified patent and that said Letters Patent is hereby corrected as shown below:

In the Claims

Claim 1, Column 37, Lines 13-37, formula (II) should read as:

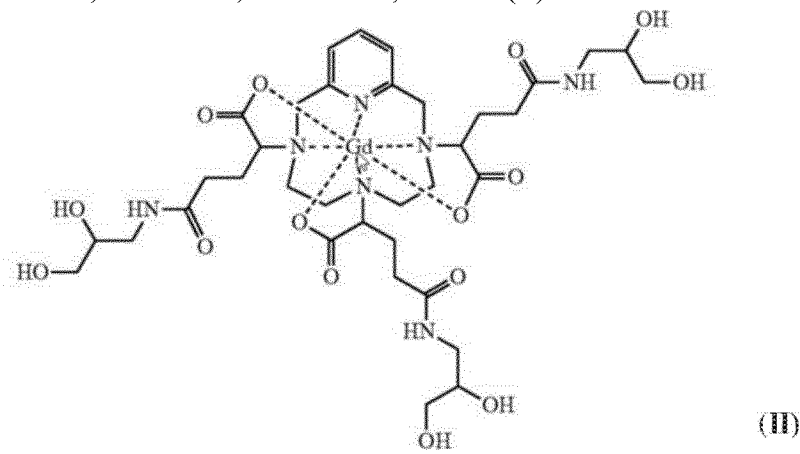

Claim 1, Column 37, Lines 43-66, formula (II-SSS) should read as:

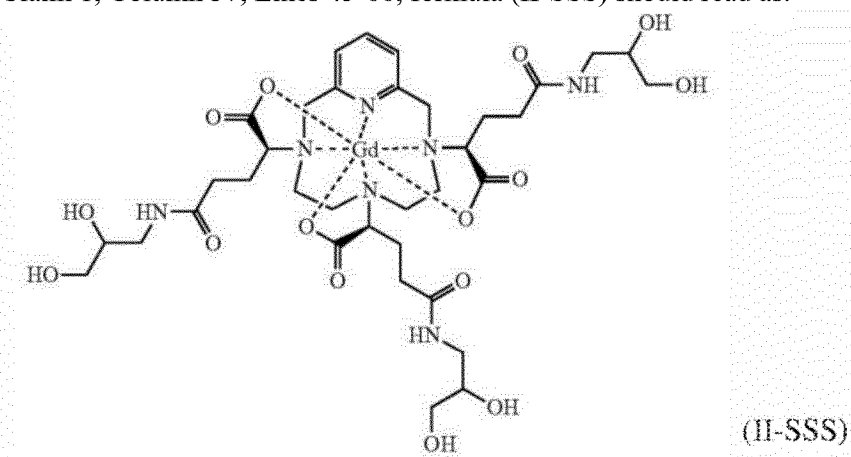

Signed and Sealed this  
Eighteenth Day of February, 2025

Coke Morgan Stewart  
*Acting Director of the United States Patent and Trademark Office*

CERTIFICATE OF CORRECTION (continued)
U.S. Pat. No. 11,426,470 B2

Claim 1, Column 38, Lines 3-25, formula (II-RRR) should read as:

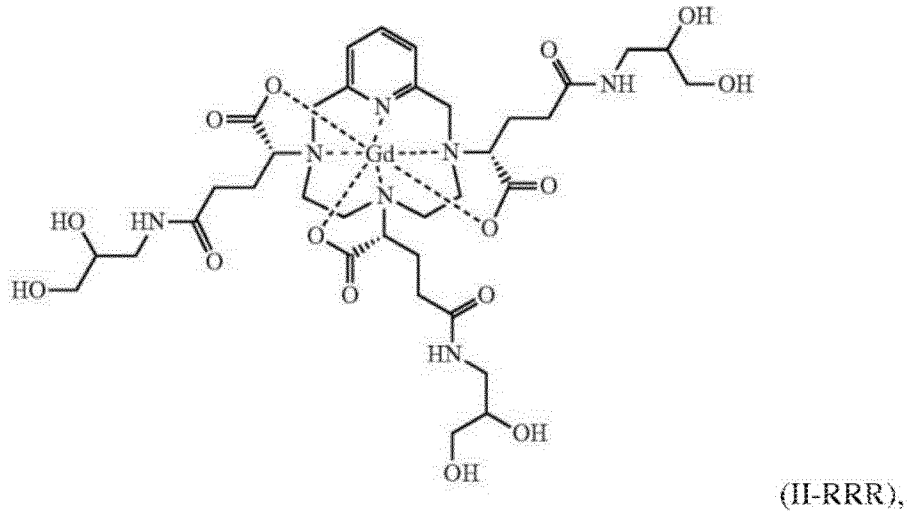

(II-RRR),